United States Patent
Ichitani

(10) Patent No.: US 10,509,023 B2
(45) Date of Patent: Dec. 17, 2019

(54) IMAGE PROCESSING APPARATUS AND COMPUTER READABLE MEDIUM FOR IMAGE PROCESSING

(71) Applicant: Konica Minolta, Inc., Tokyo (JP)

(72) Inventor: Shuji Ichitani, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 204 days.

(21) Appl. No.: 15/533,441

(22) PCT Filed: Nov. 30, 2015

(86) PCT No.: PCT/JP2015/083541
§ 371 (c)(1),
(2) Date: Jun. 6, 2017

(87) PCT Pub. No.: WO2016/093090
PCT Pub. Date: Jun. 16, 2016

(65) Prior Publication Data
US 2017/0370901 A1    Dec. 28, 2017

(30) Foreign Application Priority Data

Dec. 9, 2014  (JP) ................................ 2014-248932
Jun. 29, 2015 (JP) ................................ 2015-129678

(51) Int. Cl.
*G06T 7/11* (2017.01)
*G01N 33/483* (2006.01)
(Continued)

(52) U.S. Cl.
CPC ..... *G01N 33/4833* (2013.01); *G01N 33/5091* (2013.01); *G06T 7/0016* (2013.01); *G06T 7/11* (2017.01); *G06T 2207/30024* (2013.01)

(58) Field of Classification Search
CPC ................ G06T 7/0012; G06T 7/0083; G06T 2207/30004; G06T 7/0081;
(Continued)

(56) References Cited

U.S. PATENT DOCUMENTS 5,162,990 A * 11/1992 Odeyale .................... G06T 7/60
382/128
2011/0170786 A1  7/2011 Naini

FOREIGN PATENT DOCUMENTS

JP        2-12060 A        1/1990
JP        2004054347 A     2/2004
(Continued)

OTHER PUBLICATIONS

IPRP dated Mar. 1, 2016 from corresponding International Application No. PCT/JP2015/083541 and English translation; Total of 21 pages.
(Continued)

*Primary Examiner* — Duy M Dang
(74) *Attorney, Agent, or Firm* — Lucas & Mercanti, LLP

(57) ABSTRACT

An image processing apparatus contains an input unit to input a fluorescent image and a morphological image of a tissue. A biological substance expressed at a first structure of a cell in the tissue is stained by a fluorescent substance. The fluorescent image illustrates a fluorescent bright point which represents expression of the biological substance. The morphological image illustrates a morphology of a second structure of a cell in the tissue and contains the same range of the tissue as the fluorescent image. The apparatus further contains a feature amount extraction unit to extract a feature amount of the second structure from the morphological image, a bright point extraction unit to extract the fluorescent bright point from the fluorescent image, and a region of interest determination unit to determine a region of interest (Continued)

based on the feature amount of the second structure and a distribution of the fluorescent bright point.

17 Claims, 12 Drawing Sheets

(51) Int. Cl.
*G01N 33/50* (2006.01)
*G06T 7/00* (2017.01)

(58) Field of Classification Search
CPC ............ G06T 2207/10116; G06T 5/40; G06T 7/0085; G06T 7/60; G06T 2207/30068; G06F 19/321; A61B 5/02007; A61B 5/7264; A61B 5/742; G06K 9/4604; G06K 9/52; G06K 9/6267; G06K 9/66
See application file for complete search history.

(56) References Cited

FOREIGN PATENT DOCUMENTS

| | | |
|---|---|---|
| JP | 2006018394 A | 1/2006 |
| JP | 2006280456 A | 10/2006 |
| JP | 2013057631 A | 3/2013 |
| WO | 2013146843 A1 | 10/2013 |

OTHER PUBLICATIONS

International Search Report dated Mar. 1, 2016 for PCT/JP2015/083541 and English translation.
Extended European Search Report dated Jun. 15, 2018 from corresponding European Application No. EP 15866919.2
M. Tscherepanow et al: "Classification of Segmented Regions in Brightfield 14,15 Microscope Images", Proceedings / The 18th International Conference on Pattern Recognition, 2006 : Aug. 20-24, 2006, Hong Kong; [ICPR2006],Aug. 24, 2006 (Aug. 24, 2006), pp. 972-975.
Marcin Iwanowski et al: "Segmentation of Moving Cells in Bright Field and Epi-fluorescent Microscopic Image Sequences", Sep. 20, 2010.
JPO, Office Action for the corresponding Japanese Patent Application No. 2016-563620, dated Jul. 30, 2019, with English translation (11 pages).

* cited by examiner

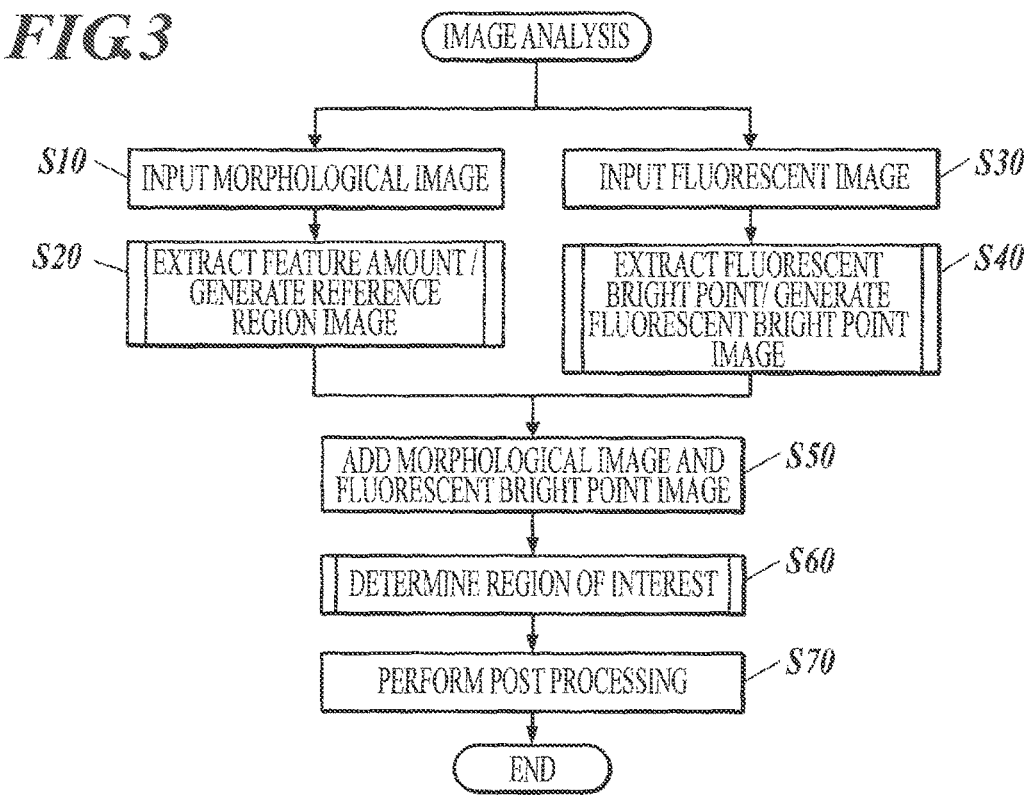
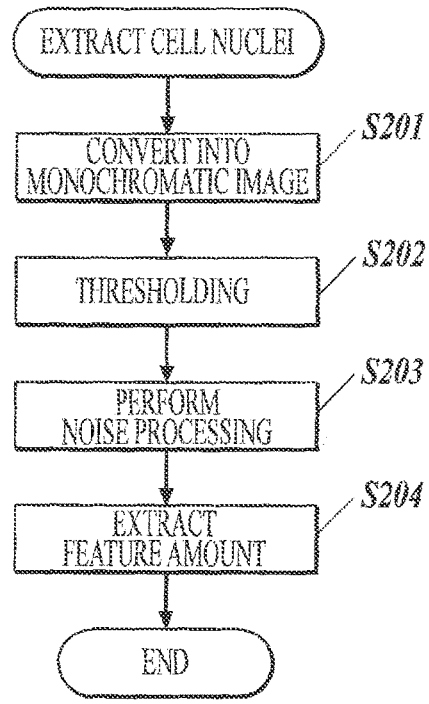

IMAGE PROCESSING APPARATUS AND COMPUTER READABLE MEDIUM FOR IMAGE PROCESSING

CROSS REFERENCE TO RELATED APPLICATION

This Application is a 371 of PCT/JP2015/083541 filed on Nov. 30, 2015, which, in turn, claimed the priority of Japanese Patent Application No. 2014-248932 filed on Dec. 9, 2014, and Japanese Patent Application No. 2015-129678 filed on Jun. 29, 2015, all applications are incorporated herein by reference.

TECHNICAL FIELD

The present invention relates to an image processing apparatus and image processing program, and particularly relates to an image processing used in the pathological diagnosis.

BACKGROUND ART

A diagnosis regarding the presence of a lesion or the kind of a lesion by observing a tissue section obtained from a human or an animal with a microscope, so called a pathological diagnosis, has been actively performed. In pathological diagnosis, first, a sampled tissue is dehydrated and blocked with paraffin to fix the tissue and cut into sections having a thickness of 2 to 8 μm, the paraffin is removed therefrom, and the sections are stained. Subsequently, an image data (a morphological image) is generated by microscopic observation. Diagnosis on the basis of the image data is performed by analyzing the changes in size and shape of a cell nucleus, morphological information such as change in tissue pattern, and staining information. It takes a lot of time and causes error for each operator to manually extract the region of observation target, such as a cell nucleus, from the morphological image. Recently, many techniques have been suggested for automatic image analysis in order to efficiently grasp a cancer region in which specific protein excessively express from the entire image of tissue section.

For example, according to the technique described in Patent Document 1, a cell nucleus region is extracted from an image, and a cell region is estimated as a circular region including a region expressing a specific protein on a cell membrane and having a predetermined radius from the center of gravity of the cell nucleus region.

The area and shape of one cell region in a tissue section can be different in morphological image according to the position to cut cells. For example, when the cells having the same size and the same shape arranged are cut by the cross section Z as in the schematic diagram in FIG. 22A, the area of cell regions are largely different from cells to cells as in FIG. 22B, which is a schematic morphological image captured from the direction orthogonal to the cross section Z. The biological substances expressed on a cell membrane are observed near the contour of each cell region as shown by ● (black circle) in FIG. 22B.

While the amount of biological substances is desired to be normalized on the basis of cell area and perimeter observed in morphological images, a cell region is determined as a circular region having a certain area according to the technique described in patent document 1. Such circular region is largely different from the actual cell region observed in the morphological image, and is not suitable for normalization on the basis of cell area.

According to the technique described in Patent Document 2, the position of cell membrane is specified on the basis of the light emission from the fluorescent substance which is used for staining cell membrane. The area and perimeter of cells can be calculated by the method in Patent Document 2.

PRIOR ART DOCUMENT

Patent Document

Patent Document 1: International Patent Application Publication No. 2013/146843
Patent Document 2: Japanese Patent Application Publication No. 2013-057631

SUMMARY OF INVENTION

Problem to be Solved by Invention

According to the technique described in Patent Document 2, however, only the cell membrane stained can be identified as the region of interest. For example, when another structure (for example, cell nucleus) in the same sample is identified as a region of interest, it takes time to obtain an image separately.

An object of the present invention is to provide an image processing apparatus and an image processing program with which it is possible to automatically extract a region of interest from cell without increasing the number of conventional steps of pathological diagnosis.

The problems to be solved by the present invention are solved by the following means.

Means for Solving the Problem

1. An image processing apparatus including:
    an input unit to input a fluorescent image and a morphological image of a tissue, wherein
      a specific biological substance expressed at a first structure of a cell in the tissue is stained by a fluorescent substance,
      the fluorescent image illustrates at least one fluorescent bright point which represents expression of the biological substance in the tissue, and
      the morphological image illustrates a morphology of a second structure of a cell in the tissue and comprises a same range of the tissue as the fluorescent image;
    a feature amount extraction unit to extract a feature amount of the second structure from the morphological image;
    a bright point extraction unit to extract the fluorescent bright point from the fluorescent image; and
    a region of interest determination unit to determine a region of interest on a basis of the feature amount of the second structure and a distribution of the fluorescent bright point.
2. The image processing apparatus according to item 1, wherein the feature amount extraction unit extracts at least one of hue, saturation, and luminance of the morphological image as the feature amount of the second structure.
3. The image processing apparatus according to item 1 or 2, wherein the region of interest determined by the region of interest determination unit includes the fluorescent bright point therein.
4. The image processing apparatus according to item 1 or 2, wherein the region of interest determined by the region of interest determination unit does not include the fluorescent bright point therein.

5. The image processing apparatus according to any one of items 1 to 4, wherein the region of interest determination unit determines the region of interest by preparing at least one candidate region based on at least the feature amount of the second structure and by integrating or dividing the candidate region on a basis of a distribution of the fluorescent bright point.

6. The image processing apparatus according to item 5, wherein the region of interest determination unit determines, as the region of interest, a region prepared by integrating the candidate region and a region surrounding the fluorescent bright points which are close to each other within a predetermined distance.

7. The image processing apparatus according to item 5, wherein the region of interest determination unit determines, as the region of interest, the candidate region divided by a line connecting the fluorescent bright points which are close to each other within a predetermined distance.

8. The image processing apparatus according to item 5, wherein the region of interest determination unit determines, as the region of interest, a region which is prepared by integration of the candidate regions within a region surrounding the fluorescent bright points which are close to each other within a predetermined distance and which does not include the fluorescent bright points therein.

9. The image processing apparatus according to item 5, wherein the region of interest determination unit determines, as the region of interest, a region at which the candidate region overlaps with a region surrounding the fluorescent bright points which are close to each other within a predetermined distance.

10. The image processing apparatus according to any one of items 1 to 9, including:
    a cell morphology extraction unit to extract the second structure of the cell from the morphological image; and
    a discrimination unit to discriminate a fluorescent bright point corresponding to the second structure on a basis of the feature amount of the second structure and a positional relation of the fluorescent bright point,
    wherein the region of interest determination unit determines the region of interest of a cell assigned to the second structure on a basis of a distribution of the fluorescent bright point corresponding to the second structure.

11. The image processing apparatus according to item 10, wherein the region of interest determination unit determines a closed curve or a polygon as the region of interest, wherein
    the closed curve or the polygon is close to or surrounds the fluorescent bright point corresponding one cell.

12. The image processing apparatus according to item 11, wherein the region of interest determination unit generates the closed curve or the polygon by using elliptical approximation using least squares method, snakes, B-spline, or polygonal approximation.

13. The image processing apparatus according to item 10, wherein the region of interest determination unit determines a dilation region as the region of interest, wherein
    the dilation region is prepared by dilation processing of the second structure and includes therein a predetermined ratio of the fluorescent bright point corresponding to the second structure.

14. The image processing apparatus according to item 13, wherein the region of interest determination unit performs the dilation processing of the second structure on a basis of a shortest distance from each of the fluorescent bright point to the second structure corresponding to the fluorescent bright point.

15. The image processing apparatus according to item 10, including a calculation unit to calculate a number of the fluorescent bright points respectively corresponding to the second structure, wherein
    when the number of the fluorescent bright points is more than a predetermined value, the region of interest determination unit determines a closed curve or a polygon as the region of interest, wherein the closed curve or the polygon is close to or surrounds the fluorescent bright point respectively corresponding the second structure, and
    when the number of the fluorescent bright points is equal to or less than the predetermined value, the region of interest determination unit determines, as the region of interest, a dilation region which is prepared by dilation processing of the second structure and which includes therein a predetermined ratio of the fluorescent bright point corresponding to the second structure.

16. The image processing apparatus according to any one of items 1 to 15, including an overlapping region assignment determination unit, wherein
    when an overlapping region is present at which a plurality of regions of interest determined by the region of interest determination unit overlap with each other, the overlapping region assignment determination unit determines, on a basis of a positional relation of the fluorescent bright point near the overlapping region and a contour of the plurality of regions of interest overlapping at the overlapping region, that the overlapping region is assigned to the region of interest near the contour of which more of the fluorescent bright points are present among the fluorescent bright points near the overlapping region.

17. An image processing program to cause a computer to function as:
    an input unit to input a fluorescent image and a morphological image of a tissue, wherein
        a specific biological substance expressed at a first structure of a cell in the tissue is stained by a fluorescent substance,
        the fluorescent image illustrates at least one fluorescent bright point which represents expression of the biological substance in the tissue, and
        the morphological image illustrates a morphology of a second structure of a cell in the tissue and comprises a same range of the tissue as the fluorescent image;
    a feature amount extraction unit to extract a feature amount of the second structure from the morphological image;
    a bright point extraction unit to extract the fluorescent bright point from the fluorescent image; and
    a region of interest determination unit to determine a region of interest on a basis of the feature amount of the second structure and a distribution of the fluorescent bright point.

Advantageous Effects of Invention

According to the present invention, it is possible to provide an image processing apparatus and an image processing program with which it is possible to automatically extract a region of interest of a cell without increasing the number of steps of conventional pathological diagnosis.

BRIEF DESCRIPTION OF DRAWINGS

FIG. 3 is a flowchart schematically showing a flow of image analysis;

FIG. 4 is a flowchart schematically showing a flow of extraction process of cell nuclei;

EMBODIMENTS FOR CARRYING OUT INVENTION

Hereinafter, preferred embodiments of the present invention are described with reference to the drawings.

<Configuration of Pathological Diagnosis Assistance System 10>

Figure 1:
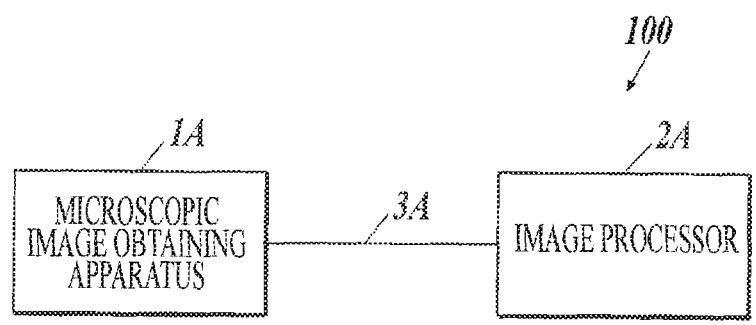
FIG. 1 is a diagram schematically showing a configuration of a pathological diagnosis assistance system.

FIG. 1 shows an example of an entire configuration of a pathological diagnosis assistance system 100.

The pathological diagnostic assistance system 100 obtains a microscopic image of a tissue section of a human body stained with a predetermined staining reagent and outputs quantified feature amount of expression of a specific biological substance in the tissue section of the observation target by analyzing the obtained microscopic image.

As shown in FIG. 1, the pathological diagnosis assistance system 100 includes a microscopic image obtaining apparatus 1A and an image processing device 2A connected to each other through an interface such as a cable 3A so as to be able to transmit and receive data.

The connecting system of the microscopic image obtaining apparatus 1A and the image processing device 2A is not particularly limited. For example, the microscopic image obtaining apparatus 1A and the image processing device 2A can be connected by a LAN (Local Area Network) or can be connected wirelessly.

The microscopic image obtaining apparatus 1A is a publically-known microscope with a camera. The microscopic image obtaining apparatus 1A obtains the microscopic image of the tissue section placed on a slide on a slide fixing stage, and transmits the image to the image processing device 2A.

The microscopic image obtaining apparatus 1A includes an irradiating unit, an image forming unit, an imaging unit, a communication I/F, etc. The irradiating unit includes a light source, filter, etc., and irradiates the tissue section placed on the slide on the slide fixing stage with light. The image forming unit includes an ocular lens, an object lens, etc., and forms an image of transmitted light or reflected light from the tissue section on the slide due to the irradiated light. The imaging unit is a camera provided in a microscope which includes a CCD (Charge Coupled Device) sensor, etc., and images an image formed on an image forming face by the image forming unit to generate digital image data of the microscopic image. The communication I/F transmits the generated image data of the microscopic image to the image processing device 2A.

The microscopic image obtaining apparatus 1A includes a bright field unit combining the irradiating unit and the image forming unit suitable for bright field observation and a fluorescent unit combining the irradiating unit and the image forming unit suitable for fluorescence observation. Both bright field observation and fluorescence observation are possible by switching the bright field unit and the fluorescence unit.

The microscopic image obtaining apparatus 1A may be any publically-known microscope (for example, phase contrast microscope, differential interference microscope, electron microscope, and the like) with a camera.

The microscopic image acquisition device 1A is not limited to a camera-attached microscope. For example, an apparatus for creating a virtual microscope slide, which scans a slide on a slide fixing stage of a microscope so as to acquire a microscopic image of the entire tissue section, can be used. (Refer to, for example, Japanese Patent Application Publication (Translation of PCT Application) No. 2002-514319). The apparatus for creating a virtual microscope slide can acquire an image data with which an image of the entire tissue section on the slide can be viewed at one time on a display unit.

The image processing device 2A analyzes the microscopic image sent from the microscopic image acquisition device 1A so as to obtain the distribution of the expressed specific biological substance in a tissue section of an observation target.

Figure 2:
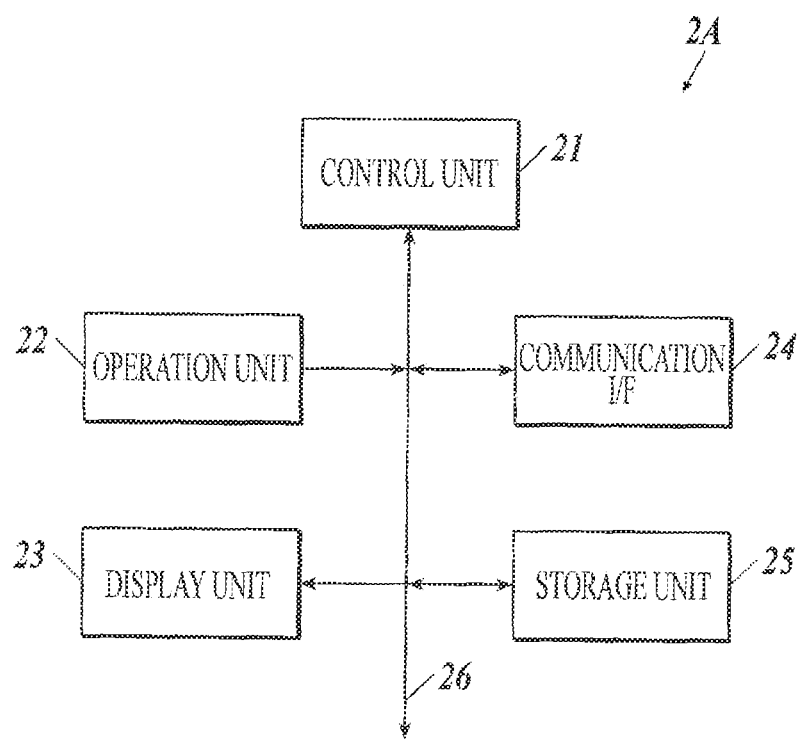
FIG. 2 is a block diagram schematically showing a functional configuration of an image processing device.

FIG. 2 shows an example of the functional configuration of the image processing device 2A.

As shown in FIG. 2, the image processing device 2A includes a control unit 21, an operation unit 22, a display unit 23, a communication I/F 24 and a storage unit 25, and these units and the like are connected to each other through a bus 26.

The control unit 21 includes a CPU (Central Processing Unit), a RAM (Random Access Memory), and the like. The control unit 21 performs a various types of processing by working together with various programs stored in the storage unit 25 and collectively controls operation of the image processing device 2A.

For example, the control unit 21 performs an image analysis (shown in FIG. 3) by working together with a program(s) stored in the storage unit 25 and functions as a feature amount extraction unit, a bright point extraction unit, a discrimination unit, a region of interest determination unit, a calculation unit, and an overlapping region assignment determination unit.

The operation unit 22 includes: a keyboard provided with character input keys; number input keys and various function keys; and a pointing device such as a mouse, and outputs press signals of the pressed keys on the keyboard and operation signals of the mouse to the control unit 21 as input signals.

The display unit 23 includes a monitor such as a CRT (Cathode Ray Tube) or an LCD (Liquid Crystal Display), and displays thereon various screens in response to instructions of display signals input from the control unit 21.

The communication I/F 24 is an interface to send/receive data to/from external devices such as the microscopic image acquisition device 1A. The communication I/F 24 functions as an input unit to input a morphological image and a fluorescence image.

The storage unit 25 includes an HDD (Hard Disk Drive) and a nonvolatile semiconductor memory. The storage unit 25 stores therein the above-described various programs, various data and so forth.

The image processing device 2A may include a LAN adapter, a router and so forth and be connected to external devices through a communication network such as a LAN.

<Images>

In the embodiment, the image processing device 2A analyzes a fluorescent image and a morphological image sent from the microscopic image acquisition device 1A. The fluorescent image represents, by fluorescent bright points, the expression of a specific biological substance which is expressed specifically at the first structure of a cell. The morphological image (for example, a bright field image) represents the second structure of a cell.

Each of the first structure and the second structure is any specific structure of a cell, for example, a cell membrane, cytoplasm, cell nucleus, and any other cell organelle. The first structure and the second structure may be the same or different with each other.

The fluorescent image shows fluorescent bright points which represent the specific biological substance expressed at the first structure of cells. A tissue section is stained by a fluorescent staining reagent including a fluorescent substance or a fluorescent substance-containing nanoparticle which specifically bonds and/or reacts with a target biological substance. The fluorescent image is a microscopic image obtained by, in the microscopic image acquisition device 1A, forming and capturing an enlarged image of the fluorescence from the fluorescent substance by irradiating an excitation light of a predetermined wavelength. The fluorescent substance-containing nanoparticle is a nanoparticle including fluorescent substance and detailed below.

The bright field image is a microscopic image acquired by, in the microscopic image acquisition device 1A, forming and capturing an enlarged image of a tissue section stained with a reagent for hematoxylin staining (H-staining reagent) or a reagent for hematoxylin-eosin staining (HE-staining reagent) with a bright field. The bright field image represents the morphology of cell(s) in the tissue section. Hematoxylin (H) is a bluish violet dye and stains cell nuclei, bony tissue, a portion of cartilaginous tissue, serous components, etc. (basophilic tissue and the like). Eosin is a red to pink dye and stains cytoplasm, connective tissue of soft tissue, red blood cells, fibrin, endocrine granules etc. (acidophilic tissue and the like).

Examples of the morphological image representing the morphology of the second structure of cell(s) can include, other than the bright field image, a fluorescent image obtained by capturing the fluorescence emitted from a fluorescent staining reagent which can specifically stain the second structure of cells and which is used to stain the tissue section. Examples of the fluorescent staining reagent used for obtaining morphological image include DAPI staining reagent for staining cell nuclei, Papanicolaou staining reagent for staining cytoplasm, and the like. Examples of the morphological image also include a phase difference image, a differential interference image, an electron microscope image, and the like.

In the pathological diagnosis, a tissue section is generally stained with HE staining reagent. Therefore, the morphological image is preferably a bright field image of an HE-stained tissue section, which expresses the morphology of cell nucleus as the second structure.

<Fluorescent Staining Reagent and Staining Method>

Hereinafter, a fluorescent staining reagent and a staining method of a tissue section using the fluorescent staining reagent are described. The fluorescent staining reagent is used for obtaining the fluorescent image representing the expression of a specific biological substance expressed specifically at the first structure of cells by fluorescent bright points.

(1) Fluorescent Substance

Examples of the fluorescent substance used in the fluorescent staining reagent include a fluorescent organic dye and a quantum dot (semiconductor particles). Preferably, the substance exhibits emission of visible to near infrared rays having a wavelength within the range from 400 to 1100 nm when excited by ultraviolet to near infrared rays having a wavelength within the range from 200 to 700 nm.

Examples of the fluorescent organic dye include fluorescein dye molecules, rhodamine dye molecules, Alexa Fluor (manufactured by Invitrogen Corporation) dye molecules, BODIPY (manufactured by Invitrogen Corporation) dye molecules, cascade dye molecules, coumarin dye molecules, eosin dye molecules, NBD dye molecules, pyrene dye molecules, Texas Red dye molecules and cyanine dye molecules.

Specific examples thereof include 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine, and Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (the above are manufactured by Invitrogen Corporation), methoxycoumalin, eosin, NBD, pyrene, Cy5, Cy5.5 and Cy7. These can be used individually, or multiple types thereof may be mixed to use.

Usable examples of the quantum dot include quantum dots respectively containing, as a component, II-VI compounds, III-V compounds, and IV elements (called "II-VI quantum dot", "III-V quantum dot" and "IV quantum dot", respectively). These can be used individually, or multiple types thereof may be mixed to use.

Specific examples thereof include but are not limited to CdSe, CdS, CdTe, ZnSe, ZnS, ZnTe, InP, InN, InAs, InGaP, GaP, GaAs, Si and Ge.

A quantum dot having a core of any of the above quantum dots and a shell provided thereon can also be used. Hereinafter, in this specification, as a notation for the quantum dot having a shell, when the core is CdSe and the shell is ZnS, the quantum dot is noted as CdSe/ZnS.

Usable examples of the quantum dot include but are not limited to CdSe/ZnS, CdS/ZnS, InP/ZnS, InGaP/ZnS, Si/SiO$_2$, Si/ZnS, Ge/GeO$_2$, and Ge/ZnS.

A quantum dot surface-treated with an organic polymer or the like may be used as needed. Examples thereof include CdSe/ZnS having a surface carboxy group (manufactured by Invitrogen Corporation) and CdSe/ZnS having a surface amino group (manufactured by Invitrogen Corporation).

(2) Fluorescent Substance-Containing Nanoparticle

The fluorescent substance-containing nanoparticles are nanoparticles in which a fluorescent substance is dispersed. The fluorescent substance and the nanoparticles may or may not be chemically bonded with each other.

The materials composing the nanoparticles are not particularly limited, and examples thereof include silica, polystyrene, polyactate acid, melamine, and the like.

The fluorescent substance-containing nanoparticles used in the embodiment can be produced by a publically-known method.

For example, fluorescent organic dye-containing silica nanoparticles can be synthesized by referring to the synthesis of FITC-containing silica nanoparticles described in Langmuir, vol. 8, page 2921 (1992). A variety of fluorescent organic dye-containing silica nanoparticles can be synthesized by using any desired fluorescent organic dye instead of FITC.

Quantum dot-containing silica nanoparticles can be synthesized by referring to the synthesis of CdTe-containing silica nanoparticles described in New Journal of Chemistry, vol. 33, page 561 (2009).

Fluorescent organic dye-containing polystyrene nanoparticles can be produced by using a copolymerization method using an organic dye having a polymerizable functional group described in U.S. Pat. No. 4,326,008 (1982) or a method of impregnating a fluorescent organic dye into polystyrene nanoparticles described in U.S. Pat. No. 5,326,692 (1992).

Quantum dot-containing polymer nanoparticles can be produced by using the method of impregnating a quantum dot into polystyrene nanoparticles described in Nature Biotechnology, vol. 19, page 631 (2001).

The average particle diameter of the fluorescent substance-containing nanoparticle is not particularly limited, and preferably, the fluorescent substance-containing nanoparticle with an average particle diameter with about 30 to 800 nm can be used. The coefficient of variation (=(standard deviation/average value)×100%) showing the variety of the particle diameter is not particularly limited, but preferably 20% or less.

The electronic microscope picture is captured using the scanning electron microscope (SEM), the cross sectional area of a sufficient number of particles is measured, and the diameter of a circle having the area of each measured value is obtained as a particle diameter. In the present embodiment, the average particle diameter is to be a calculated average of the particle diameters of 1000 particles. The coefficient of variation is also to be a value calculated from the particle diameter distribution of 1000 particles.

(3) Bonding of Biological Substance-Recognizing Portion and Fluorescent Substance-Containing Nanoparticles The biological substance-recognizing portion of the embodiment is a portion which specifically bonds and/or reacts with a target biological substance.

In the explanation of the embodiment, nanoparticles and the biological substance-recognizing portion are directly bonded with each other in advance and used as the fluorescent staining reagent which specifically bonds and/or reacts with a target biological substance. A "biological substance-recognizing portion" is a portion which specifically bonds and/or reacts with a specific biological substance.

The specific biological substance is not particularly limited as long as there is a substance specifically bonding with the specific biological substance present. Representative examples of the substance include protein (peptide), nucleic acid (oligonucleotide, polynucleotide), and the like.

Therefore, examples of the biological substance-recognizing portion include an antibody which recognizes the protein as an antigen, another protein which specifically bonds with the protein, nucleic acid including a base sequence which hybridizes with the nucleic acid, and the like.

Specific examples of the biological substance recognition portion include anti-HER2 antibody which specifically bonds with the HER2 which is a protein on the surface of the cell, anti-ER antibody which specifically bonds with the estrogen receptor (ER) in the cell nucleus, anti-actin antibody which specifically bonds with the actin forming the cytoskeleton, and the like.

Among the above, anti-HER2 antibody and anti-ER antibody bonded to the fluorescent substance-containing nanoparticle (fluorescent staining reagent) are preferable because they can be used for selecting drug administration to treat breast cancer.

The bonding form between the biological substance-recognizing portion and the fluorescent substance-containing nanoparticle is not particularly limited, and examples include, covalent bond, ionic bond, hydrogen bond, coordinate bond, physical adsorption, chemical adsorption, and the like. Bonding with strong bonding force such as covalent bond is preferable for the stability of bonding.

There can be an organic molecule connecting the biological substance-recognizing portion and the fluorescent substance-containing nanoparticle. For example, in order to suppress non-specific absorption with the biological substance, a polyethyleneglycol chain, such as SM (PEG) 12 manufactured by Thermo Scientific, can be used.

When the biological substance-recognizing portion is bonded to the fluorescent substance-containing silica nanoparticle, the same process can be applied either the fluorescent substance is the fluorescent organic dye or the quantum dot.

For example, a silane coupling agent which is a compound widely used for bonding inorganic material and organic material can be used. The silane coupling agent is a compound including an alkoxysilyl group providing a silanol group with hydrolysis in one end of the molecule and a functional group such as carboxy group, amino group, epoxy group, aldehyde group, etc. in the other end, and bonds with the inorganic material through an oxygen atom of the silanol group.

Specific examples include mercaptopropyl triethoxysilane, glycidoxypropyl triethoxysilane, aminopropyl triethoxysilane, silane coupling agent including polyethylene glycol chain (for example, PEG-silane no. SIM6492.7 manufactured by Gelest Inc.), and the like.

When the silane coupling agent can be used, two or more types can be used together.

Well-known methods can be used as the reaction method between the fluorescent organic dye-containing silica nanoparticle and the silane coupling agent.

For example, the obtained fluorescent organic dye-containing silica nanoparticle can be dispersed in pure water, the aminopropyl triethoxysilane can be added, and the above reaction can be performed at room temperature for 12 hours. After the reaction ends, by centrifugal separation or filtration, it is possible to obtain a fluorescent organic dye-containing silica nanoparticle having a surface modified with the aminopropyl group. Next, the amino group is reacted with the carboxy group in the antibody so that the antibody can bond with the fluorescent organic dye-containing silica nanoparticle through amide bond. According to necessity, condensing agent such as EDC (1-Ethyl-3-[3-Dimethylaminopropyl] carbodiimide Hydrochloride: manufactured by Pierce (Registered Trademark)) can also be used.

If necessary, a linker compound including a portion which can directly bond with the fluorescent organic dye-containing silica nanoparticle modified with the organic molecule and a portion which can bond with the molecular target substance can be used. For example, when sulfo-SMCC (Sulfosuccinimidyl 4 [N-maleimidomethyl]-cyclohexane-1-carboxylate: manufactured by Pierce) which has a portion which selectively reacts with the amino group and a portion which selectively reacts with the mercapto group is used, the amino group of the fluorescent organic dye-containing silica nanoparticle modified with aminopropyl triethoxysilane and the mercapto group in the antibody are bonded, and with this, the fluorescent organic dye-containing silica nanoparticle bonded with the antibody is made.

When the biological substance-recognizing portion is bonded to the fluorescent substance-containing polystyrene nanoparticle, the same process as the quantum dot can be applied either the fluorescent substance is the fluorescent organic dye or the quantum dot. In other words, by impregnating the fluorescent organic dye and the quantum dot in the polystyrene nanoparticle with the functional group such as the amino group, etc., it is possible to obtain the fluorescent substance-containing polystyrene nanoparticle with the functional group, and then by using the EDC or the sulfo-SMCC, the fluorescent substance-containing polystyrene nanoparticle bonded with the antibody is made.

Examples of biological substance-recognizing portion include the antibody which recognizes the following specific antigen, such as M. actin, M.S. actin, S.M. actin, ACTH, Alk-1, α1-antichymotrypsin, α1-antitrypsin, AFP, bcl-2, bcl-6, β-catenin, BCA 225, CA19-9, CA125, calcitonin, calretinin, CD1a, CD3, CD4, CD5, CD8, CD10, CD15, CD20, CD21, CD23, CD30, CD31, CD34, CD43, CD45, CD45R, CD56, CD57, CD61, CD68, CD79a, "CD99, MIC2", CD138, chromogranin, c-KIT, C-MET, collagen type IV, Cox-2, cyclin D1, keratin, cytokeratin (high molecular mass), pankeratin, pankeratin, cytokeratin 5/6, cytokeratin 7, cytokeratin 8, cytokeratin 8/18, cytokeratin 14, cytokeratin 19, cytokeratin 20, CMV, E-cadherin, EGFR, ER, EMA, EBV, VIII factor related antigen, fassin, FSH, galectin-3, gastrin, GFAP, glucagon, glycophorin A, granzyme B, hCG, hGH, *helicobacter pyroli*, HBc antigen, HBs antigen, hepatocyte specific antigen, HER2, HSV-I, HSV-II, HHV-8, IgA, IgG, IgM, IGF-1R, inhibin, insulin, kappa L chain, Ki67, lambda L chain, LH, lysozyme, macrophage, melan A, MLH-1, MSH-2, myeloperoxidase, myogenin, myoglobin, myosin, neurofilament, NSE, p27 (Kip1), p53, p53, p63, PAX 5, PLAP, *pneumocystis calini*, podoplanin (D2-40), PGR, prolactin, PSA, prostatic acid phosphatase, Renal Cell Carcinoma, S100, somatostatin, spectrin, synaptophysin, TAG-72, TdT, thyroglobulin, TSH, TTF-1, TRAcP, tryptase, villin, vimentin, WT1, Zap-70, and the like.

The fluorescent substance or the fluorescent substance-containing nanoparticle may be directly connected to the biological substance-recognizing portion as described above. Otherwise, as in the indirect method in publically-known immunological staining, the fluorescent substance or the fluorescent substance-containing nanoparticle may be bonded to the biological substance-recognizing portion indirectly in the staining step. Specifically, for example, the tissue sample is reacted with a biotinylated primary antibody with the specific biological substance as antigen, further reacted with a staining reagent including the fluorescent substance or the fluorescent substance-containing nanoparticle modified by streptavidin, so that the staining is performed by the specific bonding of streptavidin and biotin to form a complex. Furthermore, the tissue sample may be reacted with a primary antibody with the specific protein as an antigen, further reacted with a secondary biotinylated antibody with the primary antibody as an antigen, reacted with the fluorescent substance or the fluorescent substance-containing nanoparticle modified by streptavidin for staining.

(4) Staining Method

The method of creating the tissue section is not particularly limited, and the tissue section which is made by publically-known methods can be used. The staining method described below is not limited to a pathological tissue section, and can be applied to cultured cells.

(4.1) Removing Paraffin

A tissue section is immersed in a container with xylene, and paraffin is removed. The temperature is not particularly limited, and the processing can be performed at room temperature. Preferably, the immersing time is 3 minutes or more and 30 minutes or less. The xylene can be changed during the immersion as necessary.

Next, the tissue section is immersed in a container with ethanol, and the xylene is removed. The temperature is not particularly limited, and the processing can be performed at room temperature. Preferably, the immersing time is 3 minutes or more to 30 minutes or less. The ethanol can be changed during the immersion as necessary.

Next, the tissue section is immersed in a container with water to remove the ethanol. The temperature is not particularly limited, and the processing can be performed at room temperature. Preferably, the immersing time is 3 minutes or more and 30 minutes or less. The water can be changed during the immersion as necessary.

(4.2) Activating Processing

Activating process of the biological substance in the tissue section is performed according to publically-known methods.

Although the activating conditions are not specifically set, examples of liquid for activation that can be used include, 0.01M citric acid buffered solution (pH 6.0), 1 mM EDTA solution (pH 8.0), 5% urea, 0.1M tris-hydrochloric acid buffered solution. Examples of the heating device that can be used include autoclave, microwave, pressure pan, water bath, etc. The temperature is not particularly limited, and the processing can be performed at room temperature. The processing can be performed at a temperature of 50 to 130° C. and the amount of time that the processing is performed can be 5 to 30 minutes.

Next, the tissue section after activating processing is immersed in the container with PBS (Phosphate Buffered Saline), and cleaning is performed. The temperature is not limited, and the processing can be performed at room temperature. Preferably, the immersing time is 3 minutes or more to 30 minutes or less. The PBS can be changed during the immersion as necessary.

(4.3) Staining Using Fluorescent Staining Reagent

The PBS dispersion liquid of the fluorescent staining reagent is placed on the tissue section and reacted with the biological substance in the tissue section.

By changing the biological substance-recognizing portion in the fluorescent staining reagent, staining can be applied to various biological substances. When the fluorescent substance-containing nanoparticle bonded with plural types of biological substance-recognizing portion is used as the fluorescent staining reagent, the fluorescent substance-containing nanoparticle PBS dispersion liquid of each of the above can be mixed in advance, or the liquid can be sequentially placed on the tissue section separately. The temperature is not particularly limited, and the processing can be performed at room temperature. Preferably, the reacting time is 30 minutes or more to 24 hours or less.

Preferably, a publically-known blocking agent such as BSA included in PBS is dropped before staining with the fluorescent staining reagent.

Next, the tissue section after staining is immersed in the container with PBS, and the unreacted fluorescent substance-containing nanoparticle is removed. The temperature is not particularly limited, and the processing can be performed at room temperature. Preferably, the immersing time is 3 minutes or more to 30 minutes or less. The PBS can be changed during the immersion as necessary. A cover glass is placed on the tissue section to be sealed. A commercially available sealing agent can be used as necessary.

The HE staining with a HE staining reagent is performed before sealing with the cover glass.

(5) Obtaining Fluorescent Image

The microscopic image obtaining apparatus 1A is used to obtain the microscopic image (fluorescent image) of the stained tissue section with a wide visual field. In the microscopic image obtaining apparatus 1A, the excitation light source and the fluorescence detecting optical filter are selected according to the absorption maximum wavelength and the fluorescent wavelength of the fluorescent substance used in the fluorescent staining reagent.

Preferably, the visual field of the fluorescent image is 3 $mm^2$ or more, more preferably 30 $mm^2$ or more, and even more preferably 300 $mm^2$ or more.

<Operation of Pathological Diagnosis Assistance System 100 (Including the Method of Image Processing)>

Below, the operation of obtaining the above described fluorescent image in which fluorescent bright points represent the expression of a specific biological substance at the first structure of cells and the morphological image in which the second structure of cells is represented and performing analysis in the pathological diagnosis assistance system 100 is described.

<<Method of Obtaining Image>>

In the embodiment, the method of obtaining images is described. The example of the observation target here is a tissue section of a breast cancer tissue. The specific biological substance expressing at the first structure is HER2 protein at the cell membrane. The tissue section is stained with a fluorescent staining reagent including fluorescent substance-containing nanoparticles to which anti-HER2 antibody is bonded. The morphological image which represents the second structure is a bright field image obtained by capturing HE-stained bluish violet cell nuclei. A cell region enclosed by the cell membrane is extracted as a region of interest.

First, the operator stains the tissue section using two kinds of staining reagent, that is, a HE staining reagent and a fluorescent staining reagent (the fluorescent substance-containing nanoparticle bonded with anti-HER2 antibody).

Subsequently, a bright field image and a fluorescent image are obtained with the microscopic image obtaining apparatus 1A by steps (a1) to (a5).

(a1) The operator mounts the tissue section stained with the HE staining reagent and the fluorescent staining reagent on a slide, and places the slide on a slide fixing stage of the microscopic image obtaining apparatus 1A.

(a2) The bright field unit is set, the capturing magnification and focus are adjusted, and the region of the observation target in the tissue section is positioned in the visual field.

(a3) Capturing is performed with the capturing unit to generate an image data of a bright field image (a morphological image), and the image data is transmitted to the image processor 2A.

(a4) The unit is changed to the fluorescent unit.

(a5) Capturing is performed with the capturing unit without changing the visual field and the capturing magnification to generate an image data of a fluorescent image, and the image data is transmitted to the image processor 2A.

The method of obtaining images is not limited to the above method, but is suitably changed according to the kind of the morphological image. For example, when the fluorescent image is used as a morphological image, in which cell membrane is stained with a fluorescent substance, the unit is changed to the fluorescent unit. After the above (a2), a fluorescent image as a morphological image is obtained using the fluorescent unit in (a3). After changing the emission light and filter in (a4), a fluorescent image showing the expression of specific biological substance with fluorescent bright points is obtained in (a5).

The fluorescent image and the morphological image are obtained by capturing almost the same area of the tissue section According to the above method of obtaining images, however, the fluorescent image and the morphological image are not limited to the images of the same area, as long as at least a part of the captured area overlaps with each other. Specifically, a fluorescent image of a narrow area of the tissue section and a morphological image of a wide area including the area for fluorescent image can be obtained and may be used in the image analysis detailed below, after positioning of the fluorescent image and the morphological image by a publically-known method.

Subsequently, image analysis is performed in the image processor 2A on the basis of the bright field image and the fluorescent image.

FIG. 3 shows a flowchart of the image analysis in the image processor 2A.

The image analysis shown in FIG. 3 is performed by the control section 21 in coordination with the image processing program stored in the storage section 25. The control section 21 performs the processing as described below in accordance with the image processing program.

<<First Image Analysis>>

First, when the bright field image (the morphological image) is input from the microscopic image obtaining apparatus 1A through the communication I/F 24 (step S10), the feature amount of the second structure is extracted from the bright field image (step S20).

In step S20, as shown in FIG. 4, the conversion of the bright field image to the monochrome image is performed (step S201), threshold processing is performed on the monochrome image using a predetermined threshold to binarize each pixel value (step S202), and noise processing is performed on the binary image (step S203).

Specifically, the noise processing can be performed by closing process on the binary image. The closing process includes dilation process and erosion process by the same number of times. In the dilation process, the target pixel is replaced with a white pixel when any of the pixels within the range of n×n pixels (n is an integer of 2 or more) from the target pixel is white. In the erosion process, the target pixel is replaced with a black pixel when any of the pixels within the range of n×n pixels from the target pixel is black. Small regions such as noise can be removed by the closing process.

After the process of steps S201 to S203, an image (a reference region image) with a reference region(s) extracted can be generated. The reference region is a region of the second structure (cell nucleus in the embodiment) extracted from the bright field image.

Subsequently, a feature amount(s) of second structure is extracted from the bright field image on the basis of the extracted reference region (step S204: step of feature amount extraction). The examples of the feature amount of the second structure include information such as area, shape, and edge information of the reference region extracted from the bright field image, color (for example, hue, saturation, and luminance) of pixels inside and outside of the reference region in the bright field image, and the presence/absence of the structure (for example, cell nucleoli) in cell nucleus.

Figure 5:
FIG. 5 shows examples of binary images, images showing edge intensity, images showing edge angle, and images showing normal line direction of an edge, respectively obtained from a cell image of a clearly-stained cell nucleus, a cell image of one sparsely-stained cell nucleus, and a cell image of a plurality of stained cell nuclei contiguous with each other.

FIG. 5 shows examples of binary images (reference region images) generated by the step S203 and edge information of the reference region, respectively obtained from a bright field image 30 of a clearly-stained reference region (cell nucleus), a bright field image 40 of a single sparsely-stained cell nucleus, and a bright field image 50 of a plurality of stained cell nuclei contiguous with each other.

Edge information includes, for example, edge intensity, edge angle, normal line direction of an edge, and curvature at an edge calculated by the method described in WO 2014/058721.

On the other hand, as shown in FIG. 3, when a fluorescence image is input from the microscopic image acquisition device 1A through the communication I/F 24 (Step S30), the control unit 21 extracts fluorescent bright points from the fluorescence image (Step S40: step of extracting bright point).

Figure 6:
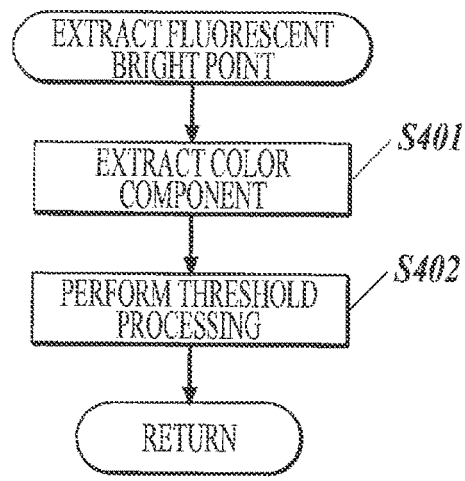
FIG. 6 is a flowchart schematically showing a flow of extraction process of fluorescent bright point.

In step S30, as shown in FIG. 6, the control unit 21 extracts a color component (step S401) from the fluorescent image according to the wavelength of the fluorescent bright points and performs threshold processing (step S402) on the fluorescent image after color component extraction to generate a binary image (fluorescent bright point image) with fluorescent bright points extracted.

In step S401, when the emission wavelength of the fluorescent particle is 550 nm, for example, only the fluorescent bright points having the emission wavelength of 550 nm are extracted in the image.

By the process in steps S401 to S402, the image with the fluorescent bright points extracted (fluorescent bright point image) can be generated.

Before the threshold processing in step S402, noise removal processing can be performed to remove the autofluorescence of cells, other components due to unnecessary signals, and the like.

After the process of steps S20 and S40, the control unit 21 performs addition processing of the reference region (cell nucleus) image and the fluorescent bright point image, to overlay the reference region image and the fluorescent bright point image (step S50).

Figure 7:
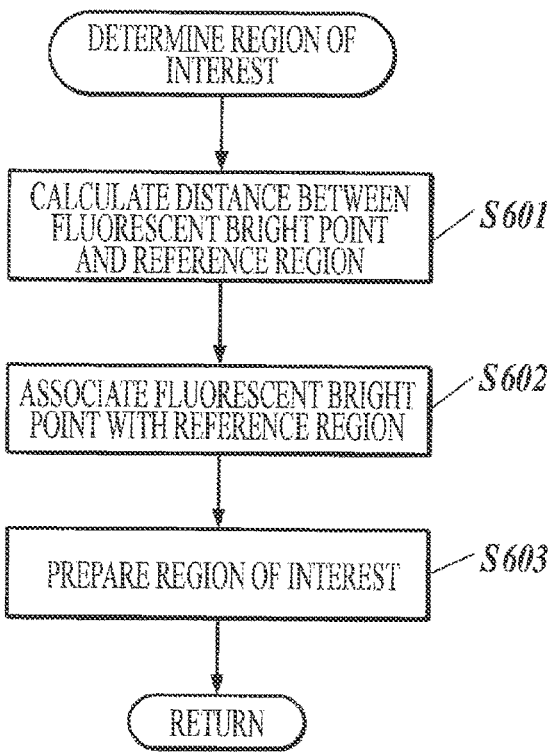
FIG. 7 is a flowchart schematically showing a flow of determination process of region of interest in first image analysis.

Subsequently, the control unit 21 determines a region of interest on the basis of the feature amount of the second structure and the fluorescent bright points (step S60: step of determining the regions of interest). FIG. 7 is a flowchart showing a process in step S60 in the first image analysis in detail. In the overlaid images after addition processing, the distances between the reference regions (cell nuclei in the embodiment) and the fluorescent bright points are respectively calculated (step S601). On the basis of the distances, the fluorescent bright points and the reference regions assigned to the same cell are associated with each other (step S602).

Figure 8A:
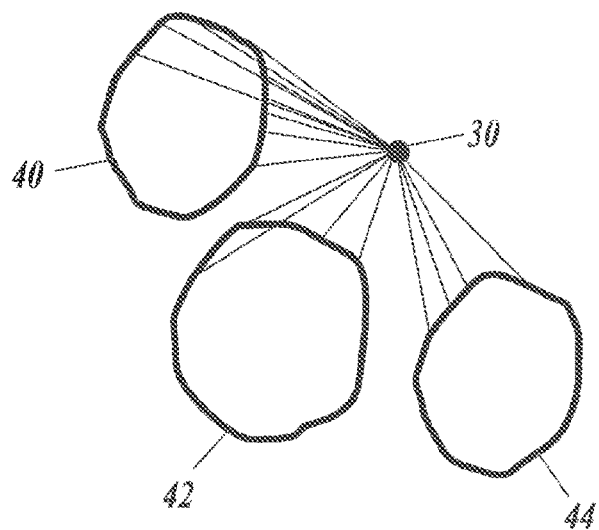
FIG. 8A is a diagram schematically explaining calculation of distance from surface of cell nuclei to a fluorescent bright point.

More specifically, in step S601, the distances are calculated from the fluorescent bright point 30 to the surface of the cell nuclei 40, 42, and 44, as shown in FIG. 8A. The calculation of the distances is conducted to all pixels on the contour of the cell nuclei 40, 42, and 44.

Figure 8B:
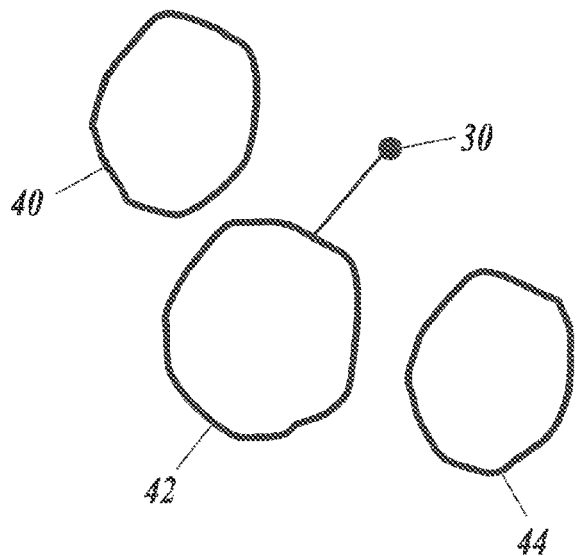
FIG. 8B is a diagram schematically showing a cell nucleus at the shortest distance from the fluorescent bright point.

In step S60, as shown in FIG. 8B, the control unit 21 determines the shortest distance from the fluorescent bright point 30 to the surface of the cell nuclei 40, 42, and 44 among the distances calculated in step S50. The control unit 21 then specifies the cell nucleus 42 as the cell nucleus nearest to the fluorescent bright point 30 and associates the fluorescent bright point 30 and the cell nucleus 42 with each other, which are assigned to the same cell. When the shortest distance from the fluorescent bright point 30 to the surface of the cell nuclei is larger than a predetermined value, the fluorescent bright point 30 may be determined as a noise, so that it is not be used after the process of step S60.

Figure 9:
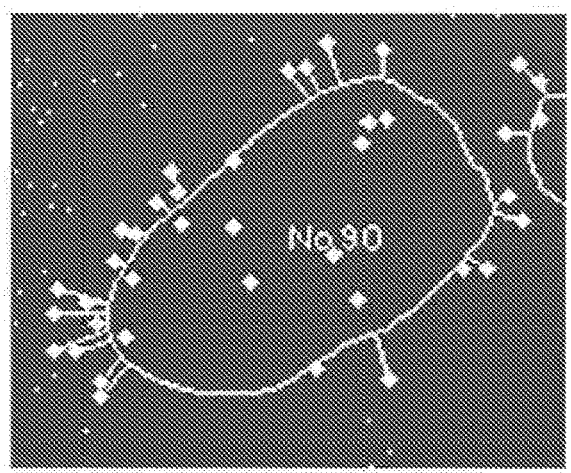
FIG. 9 is a diagram showing fluorescent bright points assigned to a cell nucleus.

FIG. 9 is a diagram showing examples of association of fluorescent bright points and reference regions, which are assigned to the same cell. The line segments respectively connect the contour of the reference regions and the fluorescent bright points associated with each other.

Subsequently, the control unit 21 determines the regions of interest in step S603.

Hereinafter, specific examples (1) to (6) of methods of determining the region of interest (cell region in the embodiment) are described with reference to the drawings. The methods are based on the position information of the fluorescent bright point associated with a reference region (cell nucleus in the embodiment). In the following specific examples, when more fluorescent bright points are associated with a cell nucleus, the shape of the obtained cell region can be closer to the actual cell.

(1) Determining Cell Region Using TOPHAT Transformation

Figure 10A:
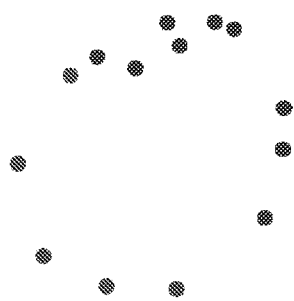
FIG. 10A is a diagram schematically showing a method of determining a cell region on the basis of the distribution of fluorescent bright points.
Figure 10B:
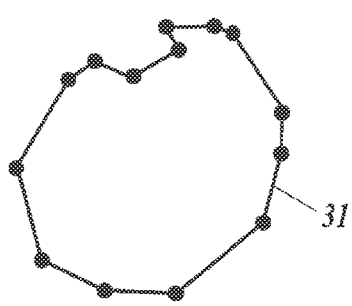
FIG. 10B is a diagram schematically showing a method of determining a cell region on the basis of the distribution of fluorescent bright points.

First, the fluorescent bright points associated with a cell nucleus shown in FIG. 10A are connected with straight lines shown in FIG. 10B, for example, to obtain a polygon 31 including the fluorescent bright points as its vertexes. Any fluorescent bright points may be connected with a straight line, however, all the fluorescent bright points preferably exist inside of the polygon 31. Subsequently, smoothing processing is performed on the polygon 31 to determine a cell region 50.

When more fluorescent bright points are associated with one cell nucleus, the deviation between the actual cell region and the obtained polygon 31 is smaller. Accordingly, the polygon 31 itself may be determined as a cell region 50 without smoothing process when the number of the fluorescent bright points is larger than the predetermined range.

Figure 10C:
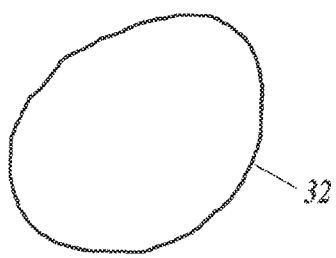
FIG. 10C is a diagram schematically showing a method of determining a cell region on the basis of the distribution of fluorescent bright points.
Figure 10D:
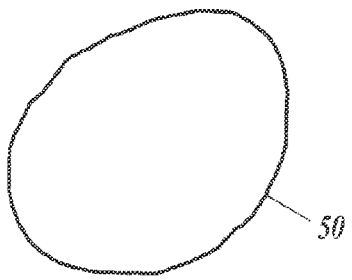
FIG. 10D is a diagram schematically showing a method of determining a cell region on the basis of the distribution of fluorescent bright points.

Smoothing processing may be performed by any method. For example, region 32 in FIG. 10C is prepared from the polygon 31 in FIG. 10B by opening processing. The region 32 is subtracted from the polygon 31 by TOPHAT transformation, so that the regions near vertexes are extracted from the polygon 31 and the pixel number X in the regions near vertexes extracted from the polygon 31 is calculated. Subsequently, dilation processing of the region 32 is performed so that the area after dilation is larger than the area before dilation processing by the area corresponding to X pixels. The region after dilation processing is determined as a cell region 50 (see FIG. 10D).

(2) Determining Cell Region Using Polygon Approximation

After preparing a polygon including the fluorescent bright points as its vertexes in FIG. 10B, for example, a predetermined shape (for example, circle, ellipse, equilateral polygon, and the like) inscribing or circumscribing the polygon may be prepared and determined as a cell region 50.

(3) Determining Cell Region by Least Squares Method

Figure 11:
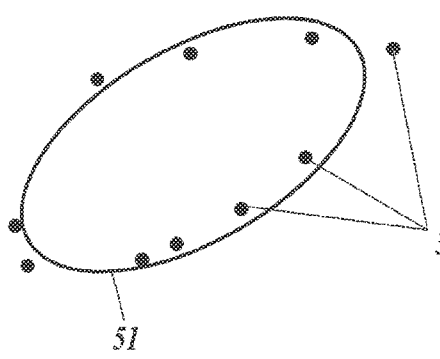
FIG. 11 is a diagram schematically showing a method of determining a cell region on the basis of the distribution of fluorescent bright points.

As shown in FIG. 11, cell region may be an ellipse 51 prepared by elliptical approximation of the coordinates of fluorescent bright points 30 associated with one cell nucleus, by least squares method using the equation of an ellipse.

(4) Determining Cell Regions Using SNAKES Processing

A cell region may be determined as a contour extracted by SNAKES processing, which is a publically-known Active Contour Model, applied to the fluorescent bright points associated with one cell nucleus.

(5) Determining Cell Regions Using B-Spline

A cell region may be determined as a B-Spline curve prepared by a publically-known method on the basis of the distribution of the fluorescent bright points associated with one cell nucleus.

(6) Determining Cell Regions Using Shape of Cell Nucleus

In addition to the position information of fluorescent bright points associated with one cell nucleus, a cell region may be determined on the basis of the shape of the cell nucleus. For example, a cell region may be prepared by dilation processing of the region of the cell nucleus.

Figure 12:
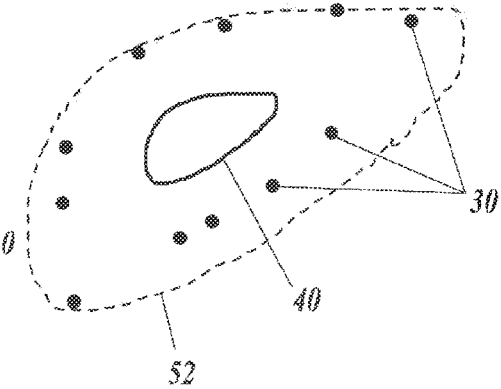
FIG. 12 is a diagram schematically showing a method of determining a cell region on the basis of the distribution of fluorescent bright points and the shape of the cell nucleus.

More specifically, for example, a cell region may be the shape 52. The shape 52 is prepared by magnifying the cell nucleus 40 shown in FIG. 12, includes all the fluorescent bright points associated with the cell nucleus 40, and has a shape similar to the cell nucleus 40.

Figure 13A:
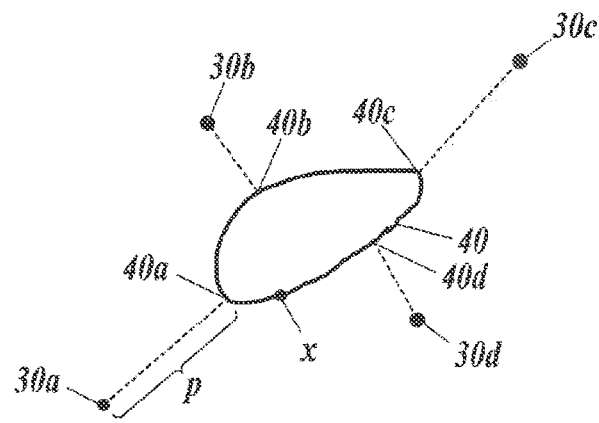
FIG. 13A is a diagram schematically showing a method of determining cell region on the basis of the distribution of fluorescent bright points and the shape of the cell nucleus.

The amount of dilation may be modified on the basis of the distances from each of the fluorescent bright points to the cell nucleus. For example, FIG. 13A illustrates cell nucleus 40 and four fluorescent bright points 30a to 30d associated with the cell nucleus 40. The control unit 21 extracts points on the cell nucleus 40 closest to each of the fluorescent bright points 30a to 30d in order to calculate the distances (amounts of dilation) from each of the fluorescent bright points 30a to 30d to the respective closest points. For example, the closest point 40a is the point closest to the fluorescent bright point 30a shown in FIG. 13A, and the amount of dilation p is the distance (the length of the dotted line in FIG. 13A) between the fluorescent bright point 30a and the closest point 40a.

Figure 13B:
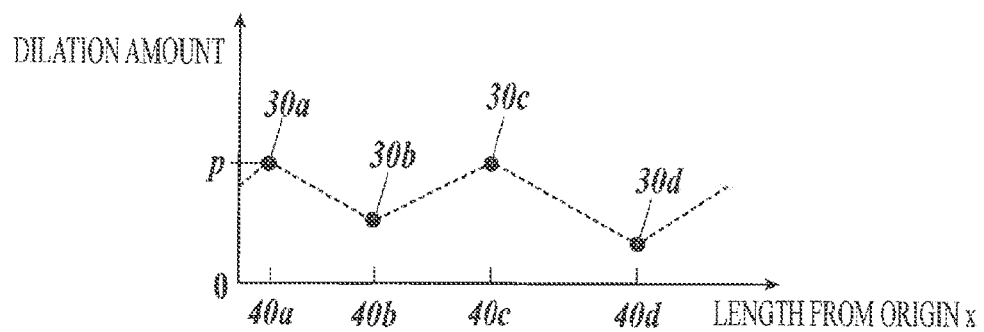
FIG. 13B is a diagram schematically showing a method of determining cell region on the basis of the distribution of fluorescent bright points and the shape of the cell nucleus.

The fluorescent bright points 30a to 30d are illustrated in FIG. 13B, for example. In the coordinate in FIG. 13B, origin x is an arbitrarily defined point on the contour of the cell nucleus 40, the length of the contour measured in a clockwise direction from the origin x to the closest points corresponding to each of the fluorescent bright points 30a to 30d is plotted on a horizontal axis, and the amount of dilation is plotted on a vertical axis. The dotted lines are prepared as shown in FIG. 13B, which interpolate between the adjacent fluorescent bright points. By reconversion to a normal orthogonal coordinate, the amount of dilation from each point on the contour of the cell nucleus 40 can be determined on the basis of the position of the observed fluorescent bright points. The dilation region thus prepared may be used as a cell region.

Figure 13C:
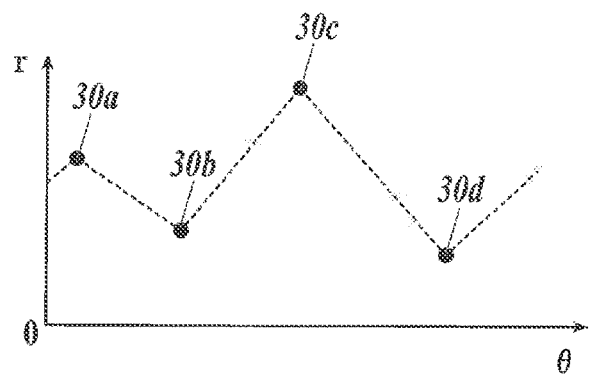
FIG. 13C is a diagram schematically showing a method of determining cell region on the basis of the distribution of fluorescent bright points and the shape of the cell nucleus.

The image of the cell nucleus 40 and the four fluorescent bright points 30a to 30d associated with the cell nucleus 40 (see FIG. 13A) may be shown on a polar coordinate as shown in FIG. 13C. In FIG. 13C, the origin is the center of the cell nucleus 40, and the dotted lines in FIG. 13C shows the interpolation between the adjacent fluorescent bright points. By reconversion to a normal orthogonal coordinate, a cell region may be prepared based on the positions of the fluorescent bright points 30a to 30d and the center of the cell nucleus 40.

The curve prepared by performing any smoothing processing on the dotted lines in FIG. 13B or FIG. 13C may be reconverted to a normal orthogonal coordinate and used as a cell region.

Any of the above methods (1) to (6) to determine cell regions in step S603 may be selected and used. When there are many fluorescent bright points associated with one cell nucleus, the methods (1) to (5) are more preferable than the method (6), because the process is relatively simple and the deviation from the actual cell region is small. Meanwhile, when there are a small number of fluorescent bright points associated with one cell nucleus, the deviation from the actual cell region by the methods (1) to (5) would be larger than the deviation by the method (6), because of the insufficient clue to determine a cell region.

Accordingly, in step S603, after calculating the number of the fluorescent bright points at first, it is preferable to prepare a cell region by the methods (1) to (5) when the calculated value is larger than a predetermined value, and to prepare a cell region by the method (6) when the calculated value is smaller than a predetermined value.

In step S603, candidate regions of a cell region may be prepared by two or more of the methods (1) to (6), respectively. The feature amount (for example, area, color, the ratio between the long diameter and the short diameter, and the like) of the candidate regions are calculated and compared with the feature amount of a standard cell of the observation target, so that the candidate region which is most likely to be a cell region is determined as a cell region.

After the process of step S603 is completed for all the fluorescent bright points and the cell nuclei associated with each other in step S602, the step returns to the process in FIG. 3. When a plurality of cell regions overlap with one another, post processing (step S70) is performed in order to assign the overlapping region to one of the overlapping regions.

Post processing may be performed by any process. For example, when the fluorescent bright points represent the expression of a specific biological substance on a cell membrane, the overlapping region is assigned to one of the cells based on the fact that fluorescent bright points are observed near the contour of cells in a tissue section.

Figure 14A:
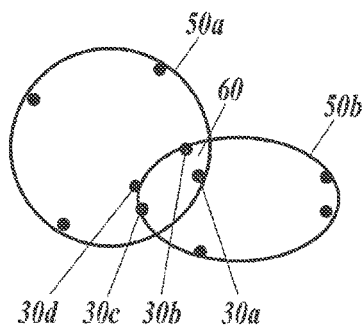
FIG. 14A is a diagram schematically showing a method of determining a cell to which an overlapping region is assigned.
Figure 14B:
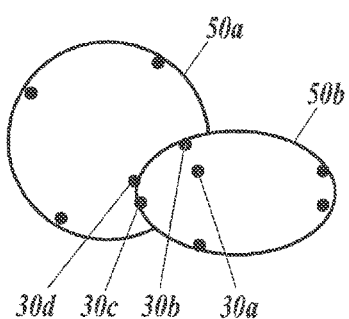
FIG. 14B is a diagram schematically showing a method of determining a cell to which an overlapping region is assigned.

More specifically, the schematic diagrams of FIG. 14A and FIG. 14B illustrates, for example, cell regions 50a and 50b overlap at the overlapping region 60. Among the fluorescent bright points 30a to 30d near the overlapping region 60, only the fluorescent bright point 30a is near the contour of the cell region 50a and the fluorescent bright points 30b to 30d are near the contour of the cell region 50b. Therefore, from the contours of the cell regions 50a and 50b surrounding the overlapping region 60, the contour of the cell region 50b is selected to be left as shown in FIG. 14B.

The distances from the fluorescent bright points 30b to 30d to the cell regions 50a and 50b may be calculated and averaged for each cell region, to determine to leave the contour of the cell region having a smaller averaged value.

According to the first image analysis, the region of interest is extracted on the basis of the distribution of fluorescent bright points associated with reference region. Therefore, the region of interest can be automatically extracted even when the region of interest cannot be directly observed in the morphological image (that is, even when the reference region is different from the region of interest).

In the above embodiment of the first image analysis, examples of the first structure, the second structure, and the region of interest are respectively a cell membrane, a cell nucleus, and a cell region, however, they are not limited by the embodiment. Any structure of a cell can be selected as the first structure, the second structure, and the region of interest.

For example, when the first structure is cytoplasm and fluorescent bright points scatter inside of the first structure, a convex closure of the fluorescent bright points associated with a reference region is prepared as the polygon in step S602. The fluorescent bright points which form vertexes of the convex closure are used for extracting the region of the first structure by performing the methods (1) to (6) in step S603 to prepare a cell region.

As explained in the above embodiment, the first image analysis is easily and preferably applied when the region of interest is the region of the first structure, however, the region of interest may be different from the region of the first structure. For example, the region of interest may be estimated and prepared on the basis of the shape of the reference region extracted in step S20 and the shape of the region of the first structure extracted in step S603. Any estimating method may be used. For example, the image processing device 2A may include a learning unit as in the second image analysis detailed below, for estimation using the features of the first structure, the second structure, and the region of interest learned in advance.

<<Second Image Anlysis>>

The image processing device 2A may include a learning unit to learn the features regarding the fluorescent bright points and the morphological image in the region of interest. The learning methods can include any methods, such as publically-known machine learning (for example, Support Vector Machine: SVM).

In the embodiment of the second image analysis described below, in the same way as the first image analysis, the first structure is cell membrane, the second structure is HE-stained cell nucleus, and the region of interest is cell region.

The second image analysis includes a learning step to calculate a learning parameter on the basis of teacher images and a process of analyzing image using the learning parameter.

The teacher images include a morphological image and a fluorescent image which are obtained by capturing a tissue sample stained in the same way as the tissue sample of the observation target. The region of interest is known in the teacher images. The kind of the captured tissue sample (for example, the kind of cell, tissue, and animal), the method of preparation, and the conditions to obtain the images are preferably the same between the teacher images and the morphological and fluorescent images for diagnosis.

(Learning Step for Calculating Learning Parameter)

In the learning step, the control unit 21 extracts feature amounts of the second structure from the morphological image input as a teacher image, as in the steps S10 to S20 in the first image analysis illustrated in the flowchart in FIG. 3.

As in the steps S30 to S40 in the first image analysis illustrated in the flowchart in FIG. 3, a fluorescent bright point image is generated from the fluorescent image input as a teacher image and feature amounts are extracted regarding the distribution of fluorescent bright points (for example, the position and the number of the fluorescent bright points).

In the learning step, the known regions of interest in the teacher images are input. Furthermore, at a random position in the teacher images is prepared "a comparative region", which is a circular region having the same area as the average area of the input regions of interest.

Subsequently, as in the step S50 in the first image analysis illustrated in the flowchart in FIG. 3, the control unit 21 performs addition processing of the morphological image and the fluorescent bright point image, and extracts feature amounts of the morphological image and the fluorescent image in the region of interest and in the comparative region, respectively. For example, the control unit 21 extracts the luminance, saturation, and edge intensity of the region of interest and the comparative region. The region of interest shows lower luminance, higher saturation, and stronger edge intensity than the comparative region, because the region of interest (cell region) in the morphological image includes a cell nucleus stained bluish violet cell nucleus in the embodiment. Furthermore, the control unit 21 calculates the minimum distance from each of the fluorescent bright points to the contour of the region of interest and to the contour of the comparative region. Many fluorescent bright points distribute at the contour of the region of interest in the fluorescent bright point image.

The control unit 21 prepares "a learning parameter" on the basis of the extracted feature amounts and stores the parameter in the storage unit 25.

The learning parameter is used for weighting according to the priority of the feature amounts. Preferably, a feature amount which is largely different between the region of interest and the comparative region is heavily weighted, because it is considered to be an important clue for determining the region of interest. For example, each feature amount is statistically tested between the region of interest and the comparative region to obtain significant probability (p value). The parameter is prepared so that the feature amount corresponding to small p-value is heavily weighed.

(Step of Image Analysis Using Learning Parameter)

In the second image analysis using the image processing device 2A including a learning unit, the processes in the steps S10 to S50 illustrated in the flowchart in FIG. 3 are performed as in the first image analysis described above. In steps S20 and S40, the control unit 21 extracts the feature amounts used for preparation of parameter in the learning step (in the embodiment, luminance of the morphological image, saturation, edge intensity, and the distribution of fluorescent bright points).

Figure 15:
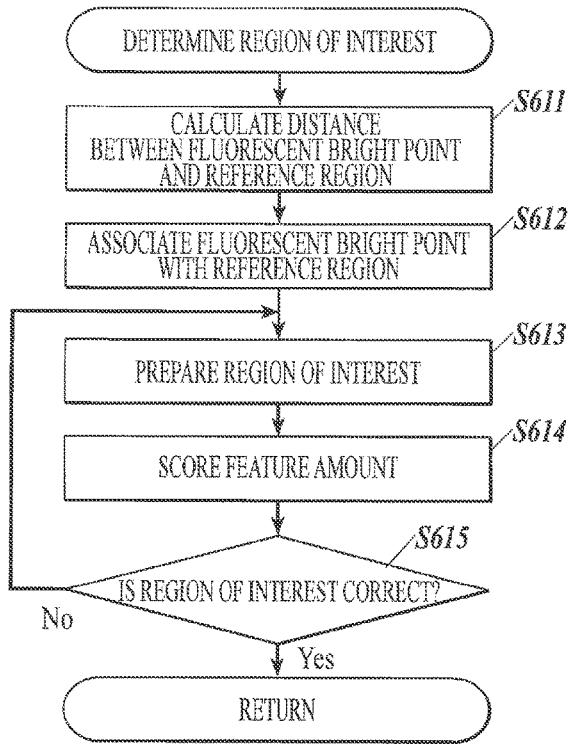
FIG. 15 is a flowchart schematically showing a flow of determination process of region of interest in second image analysis.

FIG. 15 is a flowchart showing a detailed flow of step S60 in the second image analysis. In the steps S611 to S613 in the second image analysis, the region of interest is prepared as in the steps S601 to S603 of the first image analysis.

Subsequently, the feature amounts (luminance, saturation, edge intensity, and the distribution of fluorescent bright points) of the region of interest prepared in the step S613 are scored (step S614). Any scoring method is used. For example, the control unit 21 calculates the difference between the luminance of the region of interest prepared in step S613 and the average luminance of all the regions of interest in the teacher image. The luminance score of the region of interest prepared in step S613 is determined to be +10 when the difference is small (for example, the difference is smaller than the variance of the luminance of all the region of interest in the teacher image). When the difference is larger, the luminance score is determined to be smaller.

After scoring all feature amounts, the control unit 21 reads out the learning parameter from the storage unit 25 to weigh the score of each feature amount with the learning parameter, and summarize the weighed score. On the basis of the summarized score weighed by the learning parameter, the control unit 21 determines whether the region of interest prepared in step S613 is correct or not (step S615).

When the summarized score weighed by the learning parameter is equal to or more than a predetermined value, the control unit 21 determines that the region of interest is correct (step S615: Yes), and advances to the process of step S70.

When the summarized score weighed with the learning parameter is smaller than a predetermined value, the control unit 21 determines that the region of interest is not correct (step S615: No), and returns to the process of step S613 to prepare another region of interest.

In step S70, post processing is performed as in the step S70 of the first image analysis, and image analysis is completed.

In the second image analysis, the feature amount and the parameter are changed according to the combination of the first structure, the second structure, and the region of interest.

For example, when the first structure is cytoplasm and the region of interest is a cell or a cell nucleus, at least a part of the fluorescent bright points are considered to be within the region of interest and the region of interest requires inclusion of a fluorescent bright point therein.

When the first structure is cytoplasm or cell membrane and the region of interest is a cell nucleus and the fluorescent bright points are considered not to be present within the region of interest, for example, the region of interest requires to include no fluorescent bright point and to be within a region surrounded by fluorescent bright points close to each other within a predetermined distance or fluorescent bright points assigned to one cell.

In the embodiment of the above second image analysis, the region of interest is prepared as in the steps S601 to S603 of first image analysis, however, the method to prepare the region of interest is not limited thereto. For example, the control unit 21 may prepare the candidate region on the basis of only the feature amount of the morphological image in steps S611 to S613, to discriminate whether or not correction is necessary according the fluorescent bright points in the image processing after step S614.

<<Third Image Analysis>>

The image processing device 2A may include a correction unit to divide or integrate the region of interest on the basis of the fluorescent bright points.

In the embodiment below, the third image analysis using the image processing device 2A having a division unit or an integration unit is described in the case when the specific biological substance expressed at the first structure is Ki67 protein expressed at a cell nucleus, the second structure is an HE-stained cell nucleus, and the region of interest is a cell nucleus.

In the third image analysis, the process in step S10 to S50 is performed as in the above-described first image analysis.

Figure 16:
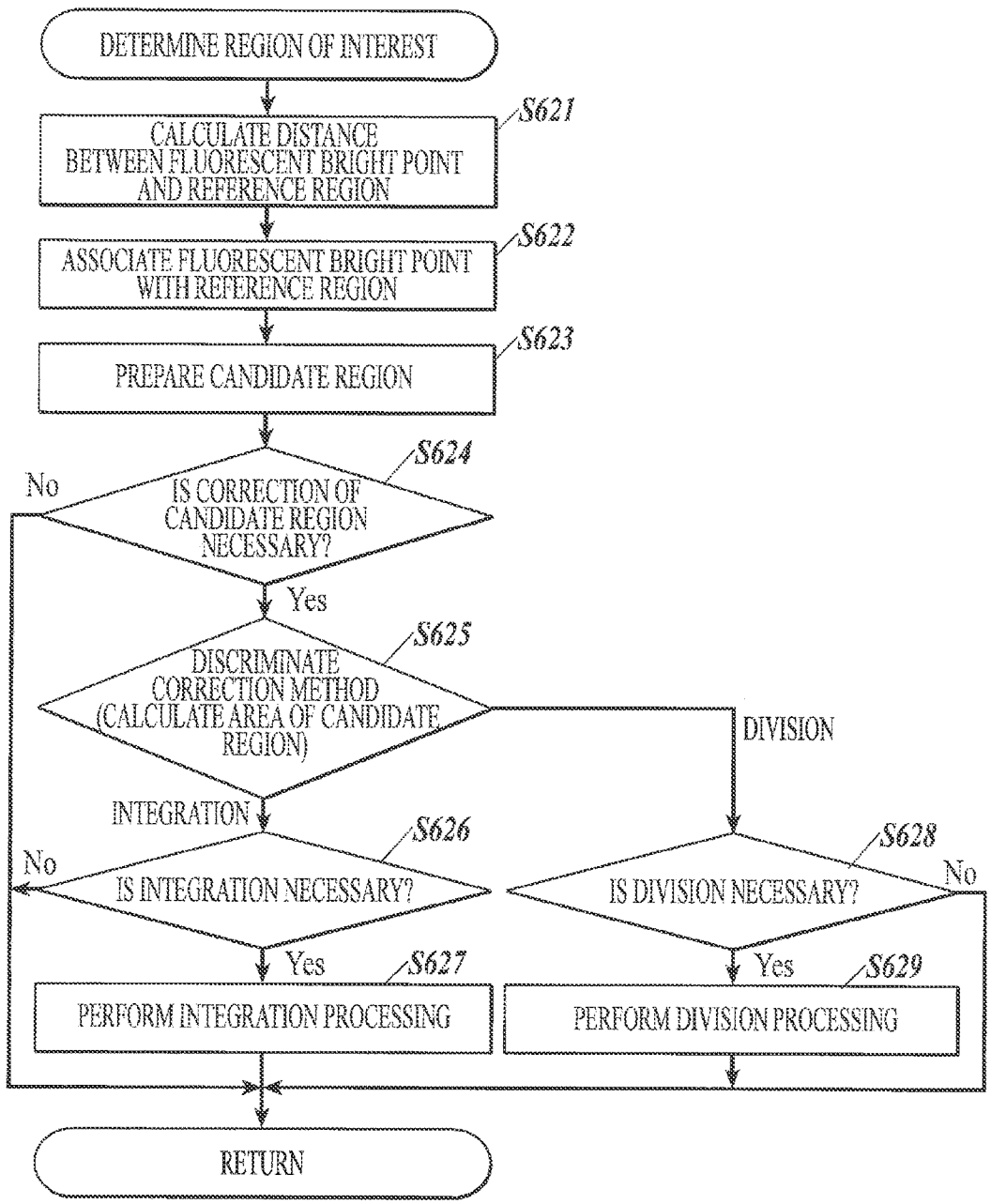
FIG. 16 is a flowchart schematically showing a flow of determination process of region of interest in second image analysis.

FIG. 16 is a detailed flowchart showing a flow of step S60 in the third image analysis. In the steps S621 to S623 in the third image analysis, a region of interest (referred to as a "candidate region" of a region of interest in the third image analysis) is prepared as in the steps S601 to S603 of the first image analysis.

Subsequently, the control unit 21 judges whether or not to correct the candidate region on the basis of the shape of the candidate region (step S624).

Figure 17A:
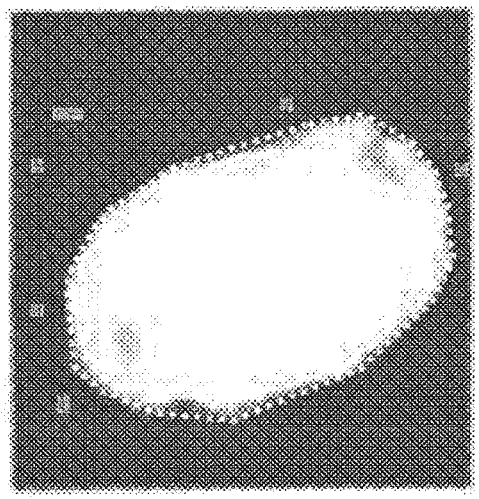
FIG. 17A is a diagram showing an example of a candidate region and a convex region.
Figure 17B:
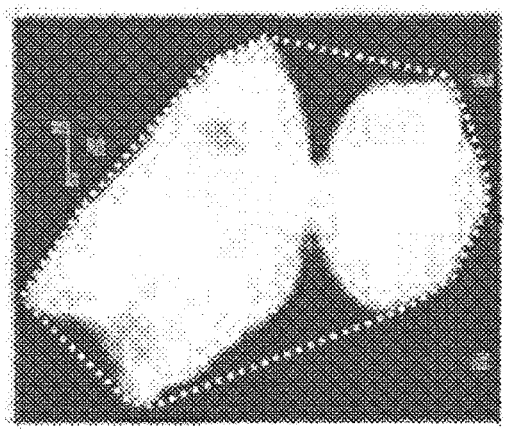
FIG. 17B is a diagram showing an example of a candidate region and a convex region.

In the step S624, for example, the judgement is based on the ratio (convex area ratio) of the candidate region area and the convex region area of the candidate region. Because of the high circularity of cell nuclei and cells, the convex area ratio is considered to be close to 1. Accordingly, when the candidate region (white region in FIG. 17A) almost corresponds to the convex region (dotted line) and the convex area ratio is close to 1, the control unit 21 judges that the correction of candidate region is not necessary (step S624: NO) because the candidate region is likely to be a region of interest, and determines the candidate region as a region of interest. Meanwhile, when the candidate region and the convex region is largely different as in FIG. 17A and the convex area ratio is not close to 1, the control unit 21 judges that the correction of the candidate region is necessary (step S624: YES) because the candidate region is not probably a region of interest, and moves to the process in step S625.

In step S624, the control unit 21 may judge whether or not correction is necessary on the basis of not only the convex area ratio, but also the area of the candidate region.

In step S625, the control unit 21 discriminates how to correct the candidate region which is judged to be in need of correction in step S624.

Figure 18A:
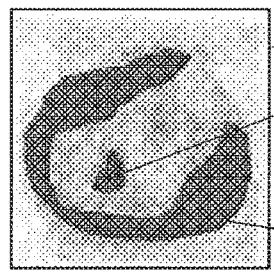
FIG. 18A is a diagram schematically explaining a method of integrating candidate regions.

In step S625, in the case of FIG. 18A for example, the control unit 21 extracts a region 80 within a certain range from the candidate region 82a, determines whether or not a plurality of small candidate regions (for example, 82a to 82b) are present in the region 80. If a plurality of small candidate regions are determined to be present in region 80, the area and/or the concentration of the candidate regions 82a to 82b in region 80 are calculated.

Subsequently, whether or not the area (total area) of candidate regions 82a to 82b is less than a certain threshold value (a condition 1-1); and/or whether the concentration of candidate regions 82a to 82b is more than a certain threshold value (a condition 1-2) or not are determined. When the conditions 1-1 and/or 1-2 are satisfied, the candidate regions 82a to 82b are determined to be in need of integration (step S625: INTEGRATION) and the processing moves to step S626.

The processing may move to step S626 either when both of the conditions 1-1 and 1-2 are satisfied or when any one of the conditions 1-1 or 1-2 is satisfied.

Figure 19A:
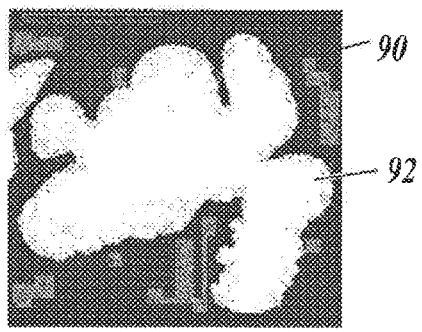
FIG. 19A is a diagram schematically explaining a method of dividing a candidate region.

Meanwhile, in the case of FIG. 19A for example, the control unit 21 extracts region 90 within a certain range from the candidate region 92, and determines whether or not one large candidate region 92 of cell nucleus is present in the region 90. If one large candidate region 92 of cell nucleus is determined to be present in region 90, the area and/or the circularity of candidate region 92 of cell nucleus in region 90 are calculated and the presence of a concave point and/or a plurality of nucleoli are detected.

Subsequently, whether or not the area of candidate region 92 is more than a certain threshold value (a condition 2-1);

whether or not the circularity of candidate region 92 is less than a certain threshold value (a condition 2-2);

whether or not a concave point is present in the candidate region 92 (a condition 2-3); and/or whether or not a plurality of nucleoli are present in the candidate region 92 (a condition 2-4)

are determined. When the conditions 2-1 to 2-4 are satisfied, the candidate region 92 is determined to be in need of division (step S625: Division) and the processing moves to step S628.

The processing may move to step S628 either when all of the conditions 2-1 to 2-4 are satisfied, when any three of the conditions are satisfied, when any two of the conditions are satisfied, or when any one of the conditions is satisfied.

In step S626, the control unit 21 judges whether or not to actually integrate the a plurality of small candidate regions of the cell nucleus based on the region information and the edge information of the candidate region (step S626).

In step S626, as shown in FIG. 18A, the control unit 21 calculates the area and/or the circularity of candidate regions 82a to 82b in the region 80. The continuity of normal line directions of the edge, the total value of angles of normal line directions of an edge, and/or curvature at the edge are calculated or detected from candidate regions 82a to 82c in the region 80, on the basis of the edge information of the candidate regions.

Subsequently, whether or not the area (total area) of candidate regions 82a to 82b is less than a certain threshold value (a condition 3-1Q);

whether or not the circularity of candidate regions 82a to 82b are less than a certain threshold value (a condition 3-2Q);

whether or not the continuity of normal line directions of the edge is present (a condition 3-3Q);

whether or not the total value of angles of normal line directions of an edge is distant from 00 (a condition 3-4Q); and/or whether or not the curvatures at the edge of candidate regions 82a to 82b are different from each other (a condition 3-5Q)

are determined. When the conditions 3-1Q to 3-5Q are satisfied, the candidate region 82 is determined to be actually in need of integration (step S626: YES) and the processing moves to step S627.

The processing may move to step S627 either when all of the conditions 3-1Q to 3-5Q are satisfied, when any four of the conditions are satisfied, when any three of the conditions are satisfied, when any two of the conditions are satisfied, or when any one of the conditions is satisfied.

Regarding the condition 3-1Q, when the area (the total area) of candidate regions 82a to 82b is small (i.e. less than the certain threshold value), it is considered that only a part of the region of interest is detected and therefore candidate regions 82a to 82b are to be integrated.

Regarding the condition 3-2Q, when the circularity of candidate regions 82a to 82b is low (i.e. lower than the certain threshold value) in spite of the high circularity of a general cell nucleus, it is considered that only a part of the region of interest is detected and therefore candidate regions 82a to 82b are to be integrated.

Regarding the condition 3-3Q, the outlines of candidate regions 82a to 82b are connected and the presence of continuity of the normal line directions (for example, the directions in the order of 0°, 90°, 180°, 270°, and 0°) obtained from the connected outlines is determined. If continuity is determined to be present, it is considered that the candidate regions 82a to 82b surrounded by the outlines are to be integrated.

Regarding the condition 3-4Q, the outlines of candidate regions 82a to 82b are connected and the rotation angle of the filter is changed from the range of 0° to 360° to the range of −180° to 0°, and further to 180°. It is determined whether the total value of angles of normal line directions of an edge goes away from 0° by the change of the rotation angle of the filter. When the total value of angles of normal line directions of an edge is determined to go away from 0°, it is considered that only a part of the region of interest is detected and therefore candidate regions 82a to 82b are to be integrated.

Regarding the condition 3-5Q, when the curvatures at the edge of candidate regions 82a to 82b are different from each other, it is considered that only a part of the region of interest is detected and therefore the candidate regions 82a to 82b are to be integrated.

Figure 18B:
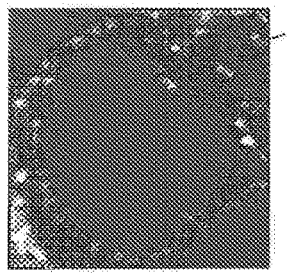
FIG. 18B is a diagram schematically explaining a method of integrating candidate regions.
Figure 18C:
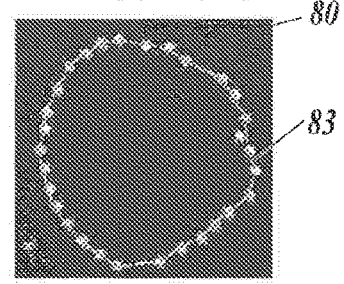
FIG. 18C is a diagram schematically explaining a method of integrating candidate regions.
Figure 18D:
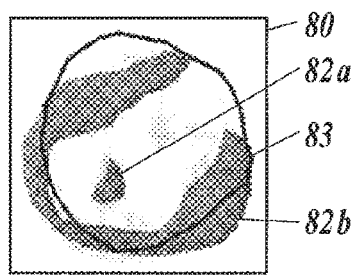
FIG. 18D is a diagram schematically explaining a method of integrating candidate regions.
Figure 18E:
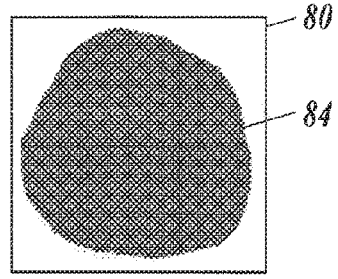
FIG. 18E is a diagram schematically explaining a method of integrating candidate regions.

In step S627, from the fluorescent image shown in FIG. 18B, the control unit 21 extracts fluorescent bright points which are close to each other within a predetermined distance and close to regions 82a and 82b. Preferably, the fluorescent bright points are associated with one cell nuclei. The control unit 21 prepares a region 83 surrounding the extracted fluorescent bright points (FIG. 18C), integrates the region 83 surrounding the extracted fluorescent bright points and the candidate regions 82a and 82b (FIG. 18D), and prepares integrated candidate region 84 (FIG. 18E).

Subsequently, the control unite 21 discriminates whether the integrated candidate region 84 satisfies the following conditions, which are similar to the conditions 3-1Q to 3-5Q:

whether or not the area (total area) of the integrated candidate region 84 is equal to or more than a certain threshold value (a condition 3-1A);

whether or not the circularity of candidate region 84 is equal to or more than a certain threshold value (a condition 3-2A);

whether or not continuity of normal line directions of the edge is present (a condition 3-3A);

whether or not the total value of angles of normal line directions of an edge is within a certain range from 0° (a condition 3-4A); and/or whether or not the curvatures at the edge of the integrated candidate region 84 becomes less scattered and is within a certain range (a condition 3-5A).

When the conditions 3-1A to 3-5A are satisfied, the integrated candidate region 84 is determined as the region of interest.

The region of interest may be determined either when all of the conditions 3-1A to 3-5A are satisfied, when any four of the conditions are satisfied, when any three of the conditions are satisfied, when any two of the conditions are satisfied, or when any one of the conditions is satisfied.

Meanwhile, in step S628, the control unit 21 judges whether to actually divide the single large candidate region of the cell nucleus or not on the basis of the region information and the edge information of the candidate region (step S628).

In step S628, the control unit 21 calculates the area and/or the circularity of the candidate region 92, and the presence of a concave point and/or a plurality of nucleoli are detected in the candidate region 92 in the region 90 in FIG. 19A. The continuity of normal line directions of the edge, the total value of angles of normal line directions of an edge, and/or curvature at the edge are calculated or detected from the candidate region 92 in the region 90, on the basis of the edge information of the candidate region.

Subsequently, whether or not the area of candidate region 92 is more than a certain threshold value (a condition 4-1Q);

whether or not the circularity of candidate region 92 is less than a certain threshold value (a condition 4-2Q);

whether or not a concave point is present in the candidate region 92 (a condition 4-3Q);

whether or not a plurality of nucleoli are present in the candidate region 92 (a condition 4-4Q);

whether or not the continuity of normal line directions of the edge is absent (a condition 4-5Q);

whether the total value of angles of normal line directions of an edge is distant from 0° (a condition 4-6Q) or not; and/or whether the curvatures at the edge of candidate region 92 are different from each other (a condition 4-7Q) or not are determined. When the conditions 4-1Q to 4-7Q are satisfied, the candidate region 92 is determined to be actually in need of division (step S628: Yes) and the processing moves to step S629.

The processing may move to step S629 either when all of the conditions 4-1Q to 4-7Q are satisfied, when any six of the conditions are satisfied, when any five of the conditions are satisfied, when any four of the conditions are satisfied, when any three of the conditions are satisfied, when any two of the conditions are satisfied, or when any one of the conditions is satisfied.

Regarding the condition 4-1Q, when the area of candidate region 92 is large (i.e. more than the certain threshold value), it is considered that a plurality of cell nuclei are detected and therefore candidate region 92 is to be divided.

Regarding the condition 4-2Q, when the circularity of candidate region 92 is low (i.e. lower than the certain threshold value) in spite of the high circularity of a general cell nucleus, it is considered that a plurality of cell nuclei are detected and therefore the candidate region 92 is to be divided.

Regarding the condition 4-3Q, when a concave point is present in the candidate region 92, and especially when concave points are present in positions opposite to each other, it is considered that a plurality of cell nuclei are detected and therefore candidate region 92 is to be divided.

Regarding the condition 4-4Q, when a plurality of nucleoli are present in the candidate region 92 although there is basically one nucleolus in one cell nucleus, it is considered that a plurality of cell nuclei are detected and therefore candidate region 92 is to be divided.

Regarding the condition 4-5Q, the outline of candidate region 92 is prepared and the absence of continuity of the normal line directions obtained from the connected outlines is determined, for example, the directions in the order of 0°, 90°, 180°, 270°, and 0°. If a continuity is determined to be absent, it is considered that the candidate region 92 surrounded by the outlines is to be divided.

For example, it is considered that the candidate region 92 is to be divided, when there are normal lines having opposite directions in the image generated by extracting normal line directions from the cell image in determining the absence of continuity of the normal line directions generated from the connected outlines of candidate region 92.

Regarding the condition 4-6Q, the outline of candidate region 92 is prepared and the rotation angle of the filter is changed from the range of 0° to 360° to the range of −180° to 0°, and further to 180°. It is determined whether the total value of angles of normal line directions of an edge goes away from 0° by the change of the rotation angle of the filter. When the total value of angles of normal line directions of an edge determined to go away from 0°, it is considered that a plurality of cell nuclei are detected and therefore candidate region 92 to be divided.

Regarding the condition 4-7Q, when the curvatures at the edge of candidate region 92 are different from each other, it is considered that a plurality of cell nuclei are detected and therefore candidate region 92 is to be divided.

Figure 19B:
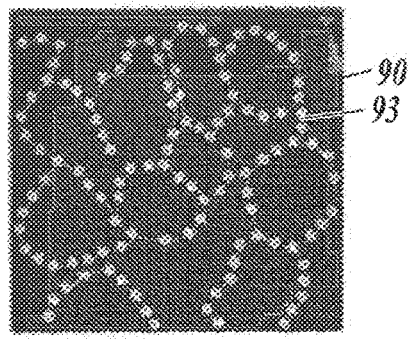
FIG. 19B is a diagram schematically explaining a method of dividing a candidate region.
Figure 19C:
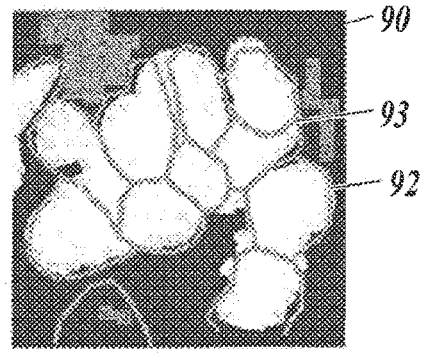
FIG. 19C is a diagram schematically explaining a method of dividing a candidate region.
Figure 19D:
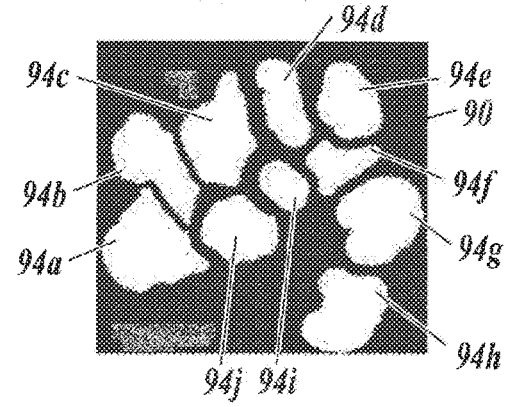
FIG. 19D is a diagram schematically explaining a method of dividing a candidate region.

In step S47, as shown in FIG. 19B, the control unit 21 prepares a line segment 93 which connects the fluorescent bright points within a predetermined distance from each other and close to the candidate region 92. The candidate region 92 is divided by the line segment 93, into divided candidate regions 94a to 94j (FIGS. 19C and 19D).

Subsequently, the control unit 21 discriminates whether the divided candidate regions 94a to 94j satisfy the following conditions, which are similar to the conditions 4-1A to 4-7A;

whether or not the area of candidate regions 94a to 94j are equal to or less than a certain threshold value (a condition 4-1A);

whether or not the circularity of candidate regions 94a to 94j are equal to or more than a certain threshold value (a condition 4-2A);

whether or not a concave point is absent in the candidate regions 94a to 94j (a condition 4-3A);

whether or not there are not more than two nucleoli present in the candidate regions 94a to 94j (a condition 4-4A);

whether or not the continuity of normal line directions of the edge is absent (a condition 4-5A);

whether the total value of angles of normal line directions of an edge is distant from 0° (a condition 4-6A) or not; and/or whether the curvatures at the edge of candidate regions 94a to 94j are different from each other (a condition 4-7A) or not are determined. When the conditions 4-1A to 4-7A are satisfied, the candidate regions 94a to 94j is determined to be regions of interest.

The region of interest may be determined either when all of the conditions 4-1Q to 4-7Q are satisfied, when any six of the conditions are satisfied, when any five of the conditions are satisfied, when any four of the conditions are satisfied, when any three of the conditions are satisfied, when any two of the conditions are satisfied, or when any one of the conditions is satisfied.

In the integration processing (step S627) in the above embodiment, the control unit 21 prepares a region 83 surrounding the fluorescent bright points, which are preferably associated with one cell nucleus and close to each other within a predetermined distance and close to (within a certain distance from) regions 82a and 82b. The control unit 21 prepares integrated candidate region 84 by integrating the region 83 and the candidate regions 82a and 82b. The method of integration is changed according to the combination of the first structure, the second structure, and the region of interest.

Figure 20A:
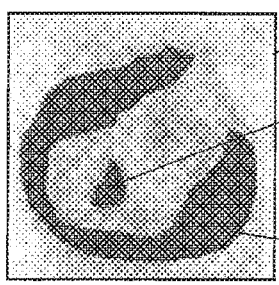
FIG. 20A is a diagram schematically explaining a method of integrating candidate regions.
Figure 20B:
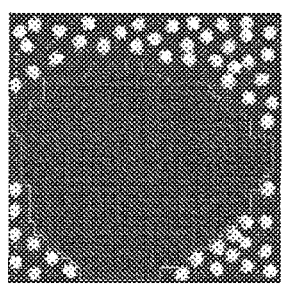
FIG. 20B is a diagram schematically explaining a method of integrating candidate regions.
Figure 20C:
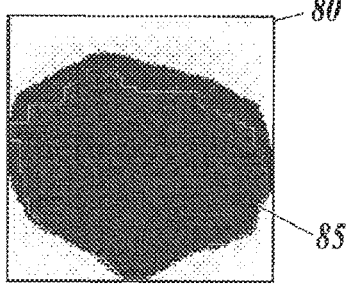
FIG. 20C is a diagram schematically explaining a method of integrating candidate regions.
Figure 20D:
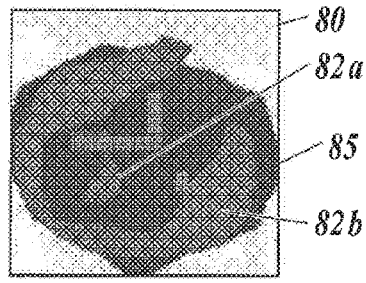
FIG. 20D is a diagram schematically explaining a method of integrating candidate regions.
Figure 20E:
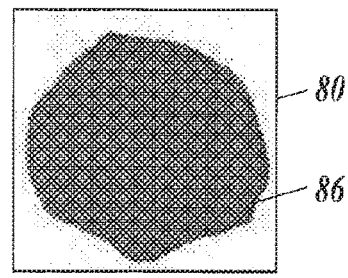
FIG. 20E is a diagram schematically explaining a method of integrating candidate regions.

For example, when the first structure is cytoplasm and the region of interest is a region of a cell nucleus, the observed fluorescent bright points are considered to scatter only outside of the region of interest as shown in FIG. 20B. In this case, the control unit 21 extracts a region 80 within a certain range from the candidate region 82a shown in FIG. 20B, and prepares a region 85 (FIG. 20C), which do not include fluorescent bright points and are surrounded by the fluorescent bright points close to each other (preferably, the fluorescent bright points are associated with one cell nucleus). Subsequently, the control unit 21 prepares an integrated candidate region 86 (FIGS. 20D and 20E) by integrating the region 85 and the regions of interest 82a and 82b, which overlap with the region 85.

In the division processing (step S629) in the above embodiment, the control unit 21 prepares the divided candidate regions 94a to 94j by a line segment 93, which connects the fluorescent bright points within a predetermined distance from each other and close to the candidate region 92. The method of division is changed according to the combination of the first structure, the second structure, and the region of interest.

Figure 21A:
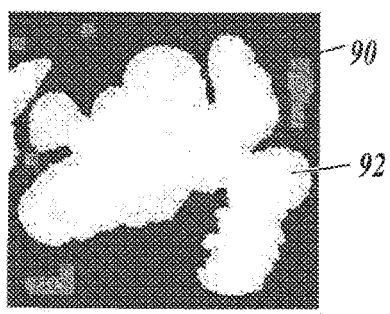
FIG. 21A is a diagram schematically explaining a method of dividing a candidate region.
Figure 21B:
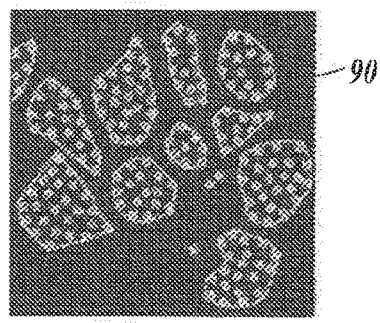
FIG. 21B is a diagram schematically explaining a method of dividing a candidate region.
Figure 21C:
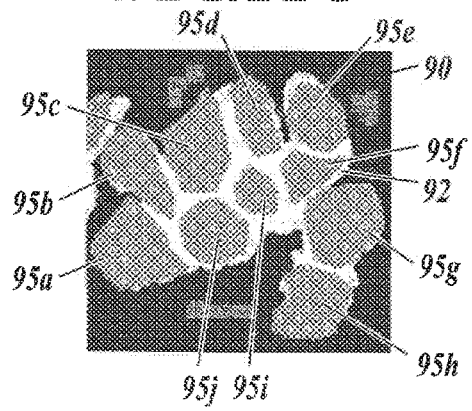
FIG. 21C is a diagram schematically explaining a method of dividing a candidate region.
Figure 21D:
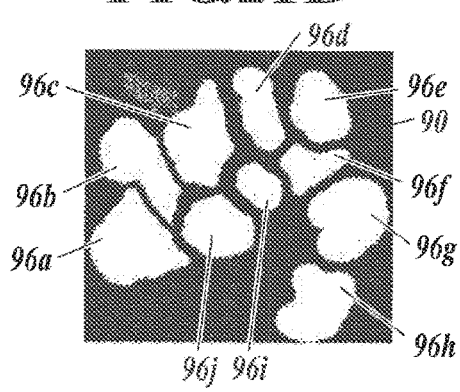
FIG. 21D is a diagram schematically explaining a method of dividing a candidate region.
Figure 22A:
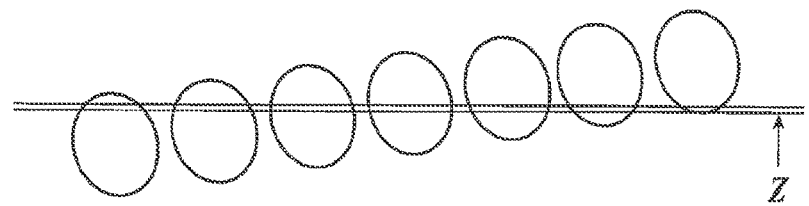
FIG. 22A is a schematic diagram showing the relation of the cutting position of cells and morphological image.
Figure 22B:
FIG. 22B is a schematic diagram showing the relation of the cutting position of cells and morphological image.

For example, when the first structure is cytoplasm and the region of interest is a region of a cell nucleus, the observed fluorescent bright points are considered to scatter within the region of interest. In this case, the control unit 21 extracts a region 90 within a certain range from the candidate region 92 as shown in FIG. 20A, groups the fluorescent bright points close to each other within a predetermined distance in the region 90 as shown in FIG. 21B, and prepares regions 95a to 95j surrounding the fluorescent bright points for each groups (FIG. 21C). The divided candidate regions 96a to 96j are determined as the overlapping regions of the candidate region 92 and each of the regions 95a to 95j (FIG. 21D).

In the above third image analysis, the candidate region is prepared as in the steps S601 to S603 of first image analysis, however, the method to prepare the region of interest is not limited thereto. For example, the control unit may prepare candidate region on the basis of only the feature amount of morphological image in steps S621 to S623, and divides or integrates using the fluorescent bright points in the image processing after step S624.

In the above embodiments, the region of interest is specified by associating the feature amount of the morphological image and the fluorescent bright points which represent the specific biological substances expressed at the first structure of cells. Therefore, even when different regions of interest are to be identified from one sample, it is not necessary to prepare morphological images for each region of interest.

In the above embodiments, on the basis of the fluorescent image, it is possible to accurately and automatically extract the region of interest, and to measure area, perimeter, and the like from a cell. This results in efficient pathological diagnosis.

Furthermore, determination of region of interest using not only the fluorescent bright points but also the feature amounts of the second structure of morphological image, the region of interest can be accurately extracted even when there are a few fluorescent bright points corresponding to one cell.

Because the method preferably used to determine the region of interest is changed according to the number of the fluorescent bright points associated with one cell, the region of interest can be determined by the most suitable method for each sample.

When the region of interest overlaps with each other, the overlapping region is assigned to any one of the overlapping cells according to the positional relation of the fluorescent bright points and the overlapping region. This results in accurate pathological diagnosis.

According to the second image analysis, probable region of interest can be selected on the basis of the feature amount of morphological image and the image including the fluorescent bright points. Accordingly, the noise can be reduced and region of interest can be accurately extracted. By weighting with learning parameters in summarizing score in step S615, the feature amount used as an important clue for determining the region of interest can be strongly reflected in determining whether the region of interest is correct or not.

When the second structure is sparsely-stained in the morphological image, one region of interest is conventionally extracted from the morphological image as divided plural regions. When the cells are present densely, overlapping and stained regions are conventionally extracted as one region. Therefore, enhancement of accuracy has been required in identifying region of interest on the basis of stained image according to the third image analysis, the candidate region can be modified by division or integration in spite of sparsely-stained or overlapping cells. Accordingly, the noise can be reduced and region of interest can be accurately extracted.

The descriptions of the embodiments are suitable examples of the present invention, and the present invention is not limited to them.

HER2 protein or Ki67 protein in breast cancer is described as the specific biological substance according to the embodiments, however, the specific biological substance is not limited to the above. It is possible to provide the physician with the feature amount quantitatively showing the expression amount of the specific protein according to the type of lesion by changing the biological substance-recognizing portion used for obtaining the fluorescent image according to the type of lesion (cancer) which is to be the target of diagnosis.

According to the embodiments, a tissue section of a human body is described as the object of the pathological diagnosis. The tissue section includes tissue culture and can be replaced with separated cells from the tissue or cultured cells.

The above description discloses an example which uses an HDD, a semiconductor nonvolatile memory, or the like as the computer readable medium of the program of the present invention, however, the present invention is not limited to the above. A portable recording medium such as a CD-ROM, etc. can be applied as other computer readable media. A carrier wave can be applied as the medium which provides the data of the program of the present invention through a communication line.

Other than the above, the detailed configuration and the detailed operation of each device composing the pathological diagnosis assistance system 10 can be suitably changed within the scope of the present invention.

INDUSTRIAL APPLICABILITY

The present invention can be preferably applied to image process for pathological diagnosis.

REFERENCE SIGNS LIST 1A microscopic image obtaining apparatus
2A image processor
3A cable
100 pathological diagnosis assistance system
21 control unit (a feature amount extraction unit, a bright point extraction unit, a discrimination unit, a region of interest determination unit, a calculation unit, and an overlapping region assignment determination unit)
22 operation unit
23 display unit
24 communication I/F
25 storage unit
26 bus
30, 30a to 30d fluorescent bright point
31 polygon
40 cell nucleus
40a closest point
50, 50a, 50b cell region
60 overlapping region
82a, 82b, 92 candidate region
83, 95a to 95j region surrounding fluorescent bright points
85 region without fluorescent bright points
84, 86 integrated candidate region
93 line segment connecting fluorescent bright points
94a to 94j, 96a to 96j divided candidate region

The invention claimed is:

1. An image processing apparatus comprising:
an input unit to input a fluorescent image and a morphological image of a tissue, wherein
a specific biological substance expressed at a first structure of a cell in the tissue is stained by a fluorescent substance,
the fluorescent image illustrates at least one fluorescent bright point which represents expression of the biological substance in the tissue, and
the morphological image illustrates a morphology of a second structure of of respective cells in the tissue and comprises a same range of the tissue as the fluorescent image;
a feature amount extraction unit to extract a feature amount of the second structure from the morphological image;
a bright point extraction unit to extract the at least one fluorescent bright point from the fluorescent image;
a discrimination unit to discriminate a fluorescent bright point of the at least one fluorescent bright point corresponding to the second structure; and
a region of interest determination unit to determine a region of interest on a basis of the feature amount of the second structure and a distribution of the fluorescent bright point corresponding to the second structure.

2. The image processing apparatus according to claim 1, wherein the feature amount extraction unit extracts at least one of hue, saturation, and luminance of the morphological image as the feature amount of the second structure.

3. The image processing apparatus according to claim 1, wherein the region of interest determined by the region of interest determination unit comprises the at least one fluorescent bright point therein.

4. The image processing apparatus according to claim 1, wherein the region of interest determined by the region of interest determination unit does not comprise the at least one fluorescent bright point therein.

5. The image processing apparatus according to claim 1, wherein the region of interest determination unit determines the region of interest by preparing at least one candidate region based on at least the feature amount of the second structure and by integrating or dividing the candidate region on a basis of a distribution of the fluorescent bright point corresponding to the second structure.

6. The image processing apparatus according to claim 5, wherein the region of interest determination unit determines, as the region of interest, a region prepared by integrating the candidate region and a region surrounding the fluorescent bright points which are close to each other within a predetermined distance.

7. The image processing apparatus according to claim 5, wherein the region of interest determination unit determines, as the region of interest, the candidate region divided by a line connecting the fluorescent bright points which are close to each other within a predetermined distance.

8. The image processing apparatus according to claim 5, wherein the region of interest determination unit determines, as the region of interest, a region which is prepared by integration of the candidate regions within a region surrounding the fluorescent bright points which are close to each other within a predetermined distance and which does not comprise the fluorescent bright points therein.

9. The image processing apparatus according to claim 5, wherein the region of interest determination unit determines, as the region of interest, a region at which the candidate region overlaps with a region surrounding the fluorescent bright points which are close to each other within a predetermined distance.

10. The image processing apparatus according to claim 1, comprising:
a cell morphology extraction unit to extract the second structure of the respective cells from the morphological image,
wherein the discrimination unit discriminates the fluorescent bright point corresponding to the second structure on a basis of the feature amount of the second structure and a positional relation of the fluorescent bright point.

11. The image processing apparatus according to claim 10, wherein the region of interest determination unit determines a closed curve or a polygon as the region of interest, wherein
the closed curve or the polygon is close to or surrounds the fluorescent bright point corresponding one cell.

12. The image processing apparatus according to claim 11, wherein the region of interest determination unit generates the closed curve or the polygon by using elliptical approximation using least squares method, snakes, B-spline, or polygonal approximation.

13. The image processing apparatus according to claim 10, wherein the region of interest determination unit determines a dilation region as the region of interest, wherein
the dilation region is prepared by dilation processing of the second structure and comprises therein a predetermined ratio of the fluorescent bright point corresponding to the second structure.

14. The image processing apparatus according to claim 13, wherein the region of interest determination unit performs the dilation processing of the second structure on a basis of a shortest distance from each of the fluorescent bright point to the second structure corresponding to the fluorescent bright point.

15. The image processing apparatus according to claim 10, comprising a calculation unit to calculate a number of the fluorescent bright points respectively corresponding to the second structure, wherein when the number of the fluorescent bright points is more than a predetermined value, the region of interest determination unit determines a closed curve or a polygon as the region of interest, wherein the closed curve or the polygon is close to or surrounds the fluorescent bright point respectively corresponding the second structure, and when the number of the fluorescent bright points is equal to or less than the predetermined value, the region of interest determination unit determines, as the region of interest, a dilation region which is prepared by dilation processing of the second structure and which comprises therein a predetermined ratio of the fluorescent bright point corresponding to the second structure.

16. The image processing apparatus according to claim 1, comprising an overlapping region assignment determination unit, wherein
when an overlapping region is present at which a plurality of regions of interest determined by the region of interest determination unit overlap with each other, the overlapping region assignment determination unit determines, on a basis of a positional relation of the fluorescent bright point near the overlapping region and a contour of the plurality of regions of interest overlapping at the overlapping region, that the overlapping region is assigned to the region of interest near the contour of which more of the fluorescent bright points are present among the fluorescent bright points near the overlapping region.

17. A computer-readable recording medium storing an image processing program to cause a computer to function as:
an input unit to input a fluorescent image and a morphological image of a tissue, wherein
a specific biological substance expressed at a first structure of a cell in the tissue is stained by a fluorescent substance,
the fluorescent image illustrates at least one fluorescent bright point which represents expression of the biological substance in the tissue, and
the morphological image illustrates a morphology of a second structure of respective cells in the tissue and comprises a same range of the tissue as the fluorescent image;
a feature amount extraction unit to extract a feature amount of the second structure from the morphological image;
a bright point extraction unit to extract the fluorescent bright point from the fluorescent image;
a discrimination unit to discriminate a fluorescent bright point of the at least one fluorescent bright point corresponding to the second structure; and
a region of interest determination unit to determine a region of interest on a basis of the feature amount of the second structure and a distribution of the fluorescent bright point corresponding to the second structure.

* * * * *